(12) United States Patent
Fukuda et al.

(10) Patent No.: US 7,951,922 B2
(45) Date of Patent: May 31, 2011

(54) PHOTORESPONSIVE HETEROCYCLIC AZO COMPOUND, METHOD FOR PRODUCING THE SAME, AND OPTICAL INFORMATION RECORDING MEDIUM

(75) Inventors: Takashi Fukuda, Tsukuba (JP); Jun Young Kim, Tsukuba (JP); Daisuke Barada, Tsukuba (JP); Nobuko Fukuda, Tsukuba (JP); Kyoko Tsuji, Tsukuba (JP); Hirobumi Ushijima, Tsukuba (JP); Kaoru Tamada, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 526 days.

(21) Appl. No.: 11/660,142

(22) PCT Filed: Aug. 12, 2005

(86) PCT No.: PCT/JP2005/015105
§ 371 (c)(1),
(2), (4) Date: May 18, 2007

(87) PCT Pub. No.: WO2006/016725
PCT Pub. Date: Feb. 16, 2006

(65) Prior Publication Data
US 2007/0242322 A1    Oct. 18, 2007

(30) Foreign Application Priority Data
Aug. 13, 2004    (JP) .................... 2004-235687

(51) Int. Cl.
C09B 29/36    (2006.01)
C09B 29/42    (2006.01)
C08F 28/06    (2006.01)
(52) U.S. Cl. .... 534/754; 534/755; 534/766; 534/DIG. 3
(58) Field of Classification Search ........................ None
See application file for complete search history.

(56) References Cited

U.S. PATENT DOCUMENTS

| | | | |
|---|---|---|---|
| 5,294,493 A | 3/1994 | Beckerbauer et al. | |
| 5,384,221 A * | 1/1995 | Savant et al. | 430/19 |
| 5,401,612 A * | 3/1995 | Etzbach et al. | 430/285.1 |
| 5,408,021 A | 4/1995 | Beckerbauer | |
| 5,461,131 A * | 10/1995 | Wiesenfeldt et al. | 526/256 |
| 5,489,451 A | 2/1996 | Omeis et al. | |
| 5,641,846 A | 6/1997 | Bieringer et al. | |
| 6,046,290 A * | 4/2000 | Berneth et al. | 526/263 |
| 6,376,655 B1 * | 4/2002 | Berg et al. | 534/573 |
| 6,620,920 B1 * | 9/2003 | Berneth et al. | 534/574 |

FOREIGN PATENT DOCUMENTS

| | | |
|---|---|---|
| JP | 5-279492 | 10/1993 |
| JP | 6-157511 | 6/1994 |
| JP | 8-109226 | 4/1996 |
| JP | 11-1688 | 1/1999 |
| JP | 11-12242 | 1/1999 |
| JP | 11-312335 | 11/1999 |
| JP | 2002-194030 | 7/2002 |
| JP | 2003-155357 | 5/2003 |
| WO | 92/10781 | 6/1992 |
| WO | WO 00/54111 | 9/2000 |
| WO | WO 00/54112 | 9/2000 |

OTHER PUBLICATIONS

Carella et al., "Polymethacrylate Copolymers Containing 4,5-Dicyanoimidazole-Based Chromophores and their Nonlinear Optical Behavior", Macromolecular Chemistry and Physics, 206, 1399-1404, Jul. 18, 2005.*
Akiyama et al., "Polymers Derived from N-Isopropylacrylamide and Azobenzene-Containing Acrylamides: Photoresponsive Affinity to Water", Journal of Polymer Science: Part A: Polymer Chemistry, 42, 5200-5214, Sep. 8, 2004.*
Fukuda, T., "Photoinduced Surface Relief Formation on Azobenzene Thin Film", Kobunshi Ronbunshu, 60(8), 428-441, 2003.*
Cui et al., "Azopyridine Side Chain Polymers: An Efficient Way to Prepare Photoactive Liquid Crystalline Materials through Self-Assembly", Chemistry of Materials, 16, 2076-2082, Apr. 29, 2004.*
Cojocariu et al., "Synthesis and Optical Storage Properties of a Novel Polymethacrylate with Benzothiazole Azo Chromophore in the Side Chain", Journal of Materials Chemistry, 14, 2909-2916, Aug. 9, 2004.*
Wang et al., "Heteroaromatic Chromophore Functionalized Epoxy-Based Nonlinear Optical Polymers", Macromolecules, 31, 4126-4134, 1998.*
Hong et al., "Optically Induced Anisotropy of Polyurethane Containing Heterocyclic Azo Chromophores", Mol. Cryst. and Liq. Cryst., 370, 181-184, 2001.*

(Continued)

Primary Examiner — Fiona T Powers
(74) Attorney, Agent, or Firm — Wenderoth, Lind & Ponack, L.L.P.

(57) ABSTRACT

There are provided a novel optical information recording material or medium excellent in various holographic optical information recording properties such as sensitivity, response speed, long-term storage stability, and repeatability, and a substance therefor. A photoresponsive heterocyclic azo compound contains an oligomer or polymer having a photoresponsive moiety in at least one of the main chain and side chain, and the photoresponsive moiety is a building block represented by the following formula (1):

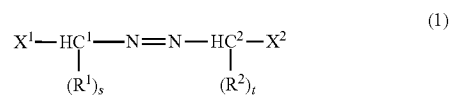

wherein $HC^1$ and $HC^2$ each represent a ring structure, at least one of them being a heterocyclic structure containing 1 or more heteroatom in the ring, $R^1$ and $R^2$ each represent a hydrogen atom or a substituent connected to the ring structure and may be the same or different ones, s and t each represent the number thereof, and $X^1$ and $X^2$ each represent a terminal group or a linking group, at least one of them being a linking group connected to the main chain of the oligomer or polymer and the terminal group being a hydrogen atom or a substituent.

14 Claims, 14 Drawing Sheets

OTHER PUBLICATIONS

Kang et al., "Light Controlled Birefringence of Liquid Crystalline Polymer Bearing an Azo Chromophore", Molecular Crystals and Liquid Crystals Science and Technology, 327, 61-64, 1999.*

Lee et al., "Liqud Crystal Alignment on a New Bifunctional Photoreactive Side-Chain Copolymer", Mol. Cryst. Liq. Cryst., 329, 321-328, 1999.*

Ringsdorf, Helmut, "Electro-Optical Effects of an Azo Dye Containing Liquid Crystalline Copolymers", Makromolekulare Chemie, 185, 1327-1334, 1984.*

Xie et al. "Recent Developments in Aromatic Azo Polymers Research" Chem. Materials. 1993 vol. 5 pp. 403-411.

Bieringer et al. "Relaxation of Holographic Gratings in Liquid-crystalline Side Chain Polymers with Azo Chromophores" Macromol. Chem. Phys. 1995 vol. 196 pp. 1375-1390.

Natansohn et al. "Azobenzene-Containing Polymers: Digital and Holographic Storage" ACS Symposium Series 1997 vol. 672 pp. 236-250.

Natansohn et al. "Molecular Addressing? Selective Photoinduced Cooperative Motion of Polar Ester Groups in Copolymers Containing Azobenzene Groups" Macromolecules 1998 vol. 31 pp. 1155-1161.

\* cited by examiner

1:1 Copolymer

2:1 Copolymer

¹H-NMR chart of A6OBCB

US 7,951,922 B2

PHOTORESPONSIVE HETEROCYCLIC AZO COMPOUND, METHOD FOR PRODUCING THE SAME, AND OPTICAL INFORMATION RECORDING MEDIUM

TECHNICAL FIELD

The present invention relates to a novel photoresponsive heterocyclic azo compound, a method for producing the same, and a rewritable optical information recording medium based thereon.

BACKGROUND ART

Society is in a highly information-oriented system, and therewith there have been increasing social demand and importance of technologies and materials for information processing and recording. However, conventional digital optical (or magnetic) recording methods are considered to have a limitation of about 1 TB/inch$^2$ even allowing for future development of technologies, and there is care that the technologies reach the limit within 5 to 10 years. Thus, it has been required to find a novel very high-density recording method, thereby establishing a technology capable of overcoming the limitation.

Holographic memories have been attracting much attention as one of ultra high-density and large capacity recording methods for meeting the demand of the society. The holographic memories can, record three-dimensional information by using light interference as it is, or convert two-dimensional planar information into a recording medium three-dimensionally. Particularly, recording and regenerating methods of two-dimensional page-data are highly compatible with signal processing systems of conventional digital recording methods and show fast transfer of the recording and regeneration, and thus have great potential and can achieve very high-capacity processing with high density exceeding 1 TB/inch$^2$.

Photorefractive materials, photopolymerizable polymers (photopolymers), and organic photochromic materials (particularly polymers) are conventionally known as optical information recording media capable for holographic memory. The pbotorefractive materials, which include inorganic crystalline materials such as barium titanate and lithium niobate as typical ones, have disadvantages of poor sensitivity, fundamental difficulty of nondestructive readout, poor selectivity for writing light wavelength, brittle, poor processabilty, difficulty for thin film fabrication, etc. Further, the photopolymers are advantageous in that they can be relatively freely designed in view of reducing the disadvantages. However, materials using the photopolymers are not rewritable and can be used only for write-once media. Known as typical examples of the organic photochromic materials are polymers having an azobenzene structure, which are capable of information recording based on various physical principles by interference exposure, multiphoton reaction, localized heat excitation, surface modification, etc., and the molecular structures and functions of the polymers have been studied For example, photo-induced birefringence, hologram recording using the same, and usability of a copolymerized macromolecule material having a photoresponsive azobenzene moiety and a highly anisotropic liquid crystalline moiety have been reported in S. Xie, A. Natansohn and P. Rochon, *Chem. Rev.*, vol. 5 (1993) p. 403-411, "*Recent Development in Aromatic Azo Polymers Research*".

Further, findings on hologram formation and relaxation dynamics in the copolymerized macromolecule material having the photoresponsive azobenzene moiety and the highly anisotropic liquid crystalline moiety have been reported in T. Bieringer, R. Wuttke, D. Haarer, U. Gesner and J. Rubner, *Macromol. Chem. Phys.*, vol. 196 (1995) p. 1375-1390, "*Relaxation of holographic gratings in liquid-crystalline side chain polymers with azo chromophores*".

Furthermore, it has been reported that, in the azobenzene polymer, the orientation of the molecules can be controlled by irradiating a linearly polarized light to utilize birefringence distribution for information recording, and the orientation can be disarranged by a circularly polarized light to erase the information. Also the effects of dipole of the highly anisotropic copolymer component on the properties have been studied in A. Natansohn and P. Rochon, ACS *Symposium Series*, vol. 672 (1997) p. 236-250, "*Azobenzene-containing polymers: digital and holographic storage*" and A. Natansohn, P. Rochon, X. Meng, C. Barrett, T. Buffeteau, S. Bonenfant and M. Pezolet, *Macromolecules*, vol. 31 (1998) p. 1155-1161, "*Molecular addressing Selective photoinduced cooperative motion of polar ester groups in copolymers containing azobenzene groups*".

Further, a holographic recording material comprising a polymer with an azobenzene structure has been applied for a patent (WO 00/54111 (JP-T-2002-539475) and WO 00/54112 (JP-T-2002-539476), the term "JP-T" as used herein means a published Japanese translation of a PCT patent application). And compounds having an azo bond like the azobenzene structure have been studied in view of wider, various applications (JP-A-11-12242, JP-A-11-1688, JP-A-6-157511, and JP-A-11-312335).

However, a material satisfying all the various properties required for a practical application such as sensitivity, response speed, long-term storage stability, and repeatability have not found in these studies and proposals.

DISCLOSURE OF INVENTION

Under the above circumstances, an object of the present invention is to provide a novel optical information recording material or medium with improved holographic, optical information recording properties such as sensitivity, response speed, long-term storage stability, and repeatability, and a substance therefor.

As a result of intense research on materials capable of high-speed recording and regenerating high-capacity data, the inventors have found that holographic, optical information recording properties such as sensitivity, response speed, long-term storage stability, and repeatability can be improved by modifying chemical structure of azobenzene compounds, which are typical and known as substances with relatively good properties, thereby developing a novel azo compound having an aromatic ring with a heteroatom. The present invention has completed based on the finding. The inventors have found that general reason why the aromatic azo compound having a heteroatom is more excellent in the properties than conventionally known azobenzene compounds are as follows.

1) The heteroatom is different from carbon in electronegativity to change the electronic structure, whereby the isomerization quantum efficiency of the photoresponsive moiety can be improved or the maximum absorption wavelength can be shortened while keeping the isomerization quantum efficiency.
2) Most of the heterocycles have a 5- or 6-membered structure while benzene ring has a 6-membered structure, whereby the number of hydrogen atoms on the ring and the bulkiness of the ring can be reduced, and thus the steric hindrance can be reduced to improve the efficiency in photoisomerization of the azo moiety.

3) The heterocycle is often free of hydrogen atoms and has unshared electron pair while the benzene ring has a 6-membered structure with hydrogen atoms on each carbon, whereby intermolecular hydrogen bonds are formed between chromophores to stably maintain the photo-induced molecule orientation.

According to the invention, there are provided the following embodiments based on the findings.

<1> A photoresponsive heterocyclic azo compound comprising an oligomer or polymer having a photoresponsive moiety in at least one of the main chain and side chain, the photoresponsive moiety being a building block represented by the following formula (1):

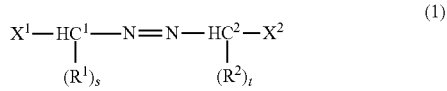

wherein $HC^1$ and $HC^2$ each represent a ring structure, at least one of them being a heterocyclic structure containing 1 or more heteroatom in the ring, $R^1$ and $R^2$ each represent a hydrogen atom or a substituent connected to the ring structure and may be the same or different ones, s and t each represent the number thereof, and $X^1$ and $X^2$ each represent a terminal group or a linking group, at least one of them being a linking group connected to the main chain of the oligomer or polymer and the terminal group being a hydrogen atom or a substituent.

<2> The photoresponsive heterocyclic azo compound according to <1>, wherein the heterocyclic structure of $HC^1$ or $HC^2$ containing 1 or more heteroatom in the ring is a 5- or 6-membered heterocyclic structure that contains 1 or more nitrogen atom, or 1 or more nitrogen atom with a sulfur atom or an oxygen atom in the ring.

<3> The photoresponsive heterocyclic azo compound according to <1> or <2>, wherein both of $HC^1$ and $HC^2$ represent the heterocyclic structure containing a heteroatom in the ring.

<4> The photoresponsive heterocyclic azo compound according to <3>, wherein one of $HC^1$ and $HC^2$ represents a 6-membered heterocyclic structure and the other represents a 5- or 6-membered heterocyclic structure.

<5> The photoresponsive heterocyclic azo compound according to any one of <1> to <4>, wherein at least one of $HC^1$ and $HC^2$ is a 5-membered heterocyclic structure selected from the group consisting of pyrrole, imidazole, pyrazole, triazole, thiophene, thiazole, thiadiazole, furan, oxazole, and isoxazole structures, which may be hydrogenated.

<6> The photoresponsive heterocyclic azo compound according to any one of <1> to <5>, wherein at least one of $HC^1$ and $HC^2$ is a 6-membered heterocyclic structure selected from the group consisting of pyridine, diazine, triazine, thiopyran, thiazine, thiadiazine, pyran, and oxazine structures, which may be hydrogenated.

<7> The photoresponsive heterocyclic azo compound according to <1>, wherein the linking group is selected from the group consisting of ester, thioester, ether, thioether, amine, amide, sulfone, sulfonyl, sulfonamide, imine, azo, and hydrocarbon chain groups, and combinations thereof.

<8> The photoresponsive heterocyclic azo compound according to <1> or <7>, wherein the oligomer or polymer connected to the linking group has the main chain of a carbon chain and the side chain having the building block represented by the formula (1).

<9> The photoresponsive heterocyclic azo compound according to <8>, wherein the carbon chain of the main chain is formed by polymerization of a monomer having the building block represented by the formula (1) and a polymerizable group or by copolymerization of the monomer and another monomer having a polymerizable group.

<10> The photoresponsive heterocyclic azo compound according to <9>, wherein the carbon chain is formed by polymerization or copolymerization of a monomer represented by the following formula (2):

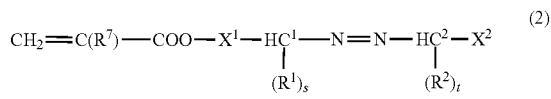

wherein $HC^1$, $HC^2$, $R^1$, $R^2$, s, t, $X^1$, and $X^2$ are as defined above, and $R^7$ represents a hydrogen atom or a methyl group.

<11> A method for producing the photoresponsive heterocyclic azo compound according to any one of <1> to <10> comprising polymerization of a polymerizable monomer or oligomer for connecting the building block of the formula (1) with the linking group.

<12> A method for producing the photoresponsive heterocyclic azo compound according to any one of <1> to <8> comprising a reaction of a compound having a reactive moiety for linking the building block of the formula (1) with an oligomer or polymer.

<13> The photoresponsive heterocyclic azo compound according to any one of <1> to <10>, wherein the side chain has at least one of a liquid crystalline group for promoting photo-induced molecular reorientation or a stabilizing group thereof, an optically anisotropic group, and a group for increasing photo-induced birefringence.

<14> A method for producing the photoresponsive heterocyclic azo compound according to <13> comprising copolymerization of a polymerizable monomer or oligomer for linking the building block of the formula (1) with a monomer or oligomer having the liquid crystalline group for promoting photo-induced molecular reorientation or the stabilizing group thereof, the optically anisotropic group, or the group for increasing photo-induced birefringence.

<15> A method for producing the photoresponsive heterocyclic azo compound according to <13> comprising a reaction of a compound having the liquid crystalline group for promoting photo-induced molecular reorientation or the stabilizing group thereof, the optically anisotropic group, or the group for increasing photo-induced birefringence with an oligomer or polymer having the building block of the formula (1) in at least one of the main chain and side chain.

<16> An optical information recording material comprising the photoresponsive heterocyclic azo compound according to any one of <1> to <10>, wherein the material records an optical information utilizing change of an optical absorption property or refractive index by light irradiation or localized heating, and the material uses the building block represented by the formula (1) as a photoresponsive moiety.

<17> The optical information recording material according to <16>, wherein the material is used as a rewritable volume hologram memory.

<18> The optical information recording material according to <16>, wherein the material is used as a rewritable surface relief memory.

According to the present invention, holographic optical information recording properties such as sensitivity, response speed, long-term storage stability, and repeatability can be remarkably improved and increased, and there is provided the high-performance optical information recording material or medium.

BEST MODE FOR CARRYING OUT THE INVENTION

Figure 1:
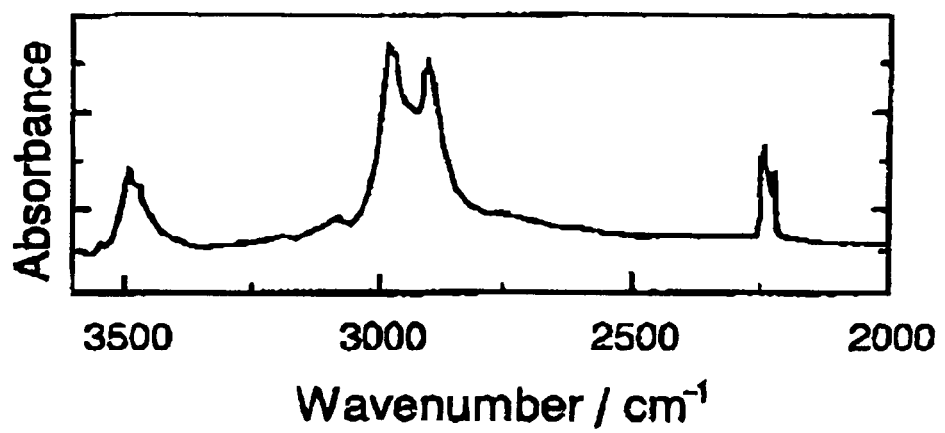
FIG. 1 is the IR spectrum of Molecule 2 of Example 1.

The present invention provides the above photoresponsive heterocyclic azo compound comprising the oligomer or polymer having the building block represented by the formula (1) in at least one of the main chain and side chain, and further provides the photoresponsive heterocyclic azo compound comprising the side chain having at least one of a liquid crystalline group for promoting photo-induced molecular reorientation or a stabilizing group thereof, an optically anisotropic group, and a group for increasing the photo-induced birefringence.

In the photoresponsive heterocyclic azo compound, at least one of $HC^1$ and $HC^2$ in the formula (1) represents a ring structure containing at least one heteroatom as a ring atom.

One of $HC^1$ and $HC^2$ may be a monocyclic or polycyclic carbon ring with no heteroatom in the ring such as an aromatic ring (e.g. benzene, naphthalene, biphenyl, etc.) and an aliphatic ring (e.g. cyclohexane), the other being a monocyclic or polycyclic, heterocyclic structure containing a heteroatom in the ring. Both $HC^1$ and $HC^2$ may be a heterocyclic structure containing a heteroatom in the ring.

In the invention, the ring structures are preferably 5- or 6-membered ring though not restrictive. Preferred embodiments a) to f) of the ring structures are described below.

a) The ring structure of $HC^1$ or $HC^2$ containing a heteroatom in the ring is a 5- or 6-membered heterocyclic structure that contains 1 or more nitrogen atom, or 1 or more nitrogen atoms with a sulfur atom or an oxygen atom in the ring.

b) Both of $HC^1$ and $HC^2$ represent the heterocyclic structure having a heteroatom in the ring.

c) One of $HC^1$ and $HC^2$ represents a 6-membered heterocyclic structure and the other represents a 5- or 6-membered heterocyclic structure.

d) At least one of $HC^1$ and $HC^2$ is a 5-membered heterocyclic structure selected from the group consisting of pyrrole, imidazole, pyrazole, triazole, thiophene, thiazole, thiadiazole, furan, oxazole, and isoxazole structures, which may be hydrogenated.

e) At least one of $HC^1$ and $HC^2$ is a 6-membered heterocyclic structure selected from the group consisting of pyridine, diazine, triazine, thiopyran, thiazine, thiadiazine, pyran, and oxazine structures, which may be hydrogenated.

f) One of $HC^1$ and $HC^2$ is the heterocyclic structure, the other being an aromatic ring.

In the formula (1), $R^1$ and $R^2$ each represent a hydrogen atom or a substituent and are connected to $HC^1$ and $HC^2$ within the range of the numbers s and t. $R^1$ and $R^2$ may be various substituents selected from the following examples, which are equal to those of the terminal groups of $X^1$ and $X^2$.

The examples include halogen atoms such as —F, —Cl, —Br, and —I; —CN; —NO$_2$; alkyl, cycloalkyl, or aryl groups such as —CH$_3$, —C$_2$H$_5$, —C$_6$H$_{13}$, and —C$_6$H$_6$; halogenated alkyl cycloalkyl, or aryl groups such as —CF$_3$, —CCl$_3$, and —C$_6$H$_5$Cl; —N$^+$(CH$_3$)$_3$; —S$^+$(CH$_3$)$_3$; substituted or unsubstituted amino groups such as —NH$_2$ and —N(CH$_3$)$_2$; —SH; —OH; alkoxy or acyl groups such as —OCH$_3$, —OC$_6$H$_5$, and —OCOCH$_3$; etc.

Preferred examples of the linking groups of $X^1$ and $X^2$ include ester groups such as —CO—O— and —O—CO—; thioester groups; —CO—; —O—; —S—; —NR$^3$—; —CO—NR$^3$—; —NR$^3$—CO—; —SO$_2$—; —SO$_2$—O—; —SO$_2$—NR$^3$—; —CR$^4$R$^5$—; —CR$^4$=CR$^5$—; —C≡C—; —C(NR$^6$)—; —CR$^6$=N—; —CR$^6$=N—NR$^3$—; —CR$^6$—NR$^6$—NR$^3$—NR$^3$—; —CR$^6$=N—CO—; —NH—NH—; —N=N—; C$_1$ to C$_{20}$ alkylene groups; C$_3$ to C$_{10}$ cycloalkylene groups; C$_6$ to C$_{10}$ arylene groups; and combinations thereof.

Herein examples of $R^3$ and $R^6$ include C$_1$ to C$_{20}$ alkyl groups, C$_3$ to C$_{10}$ cycloalkyl groups, C$_2$ to C$_{20}$ alkenyl groups, and C$_6$ to C$_{10}$ aryl groups, and examples of $R^4$ and $R^5$ include a hydrogen atom, halogen atoms, C$_1$ to C$_{10}$ alkyl groups, C$_1$ to $C_{20}$ alkoxy groups, $C_3$ to $C_{10}$ cycloalkyl groups, $C_2$ to $C_{20}$ alkenyl groups, and $C_6$ to $C_{10}$ aryl groups.

In the photoresponsive heterocyclic azo compound having the moiety represented by the formula (1), the oligomer or polymer connected to the linking group is preferably such that the main chain is a carbon chain and the side chain contains the building block of the formula (1), and the carbon chain of the main chain is preferably formed by polymerization of a monomer having the building block of the formula (1) and a polymerizable group, or by copolymerization of this monomer and another monomer having a polymerizable group.

Further, the chain may be formed by polymerization or copolymerization of the monomer represented by the formula (2).

The photoresponsive heterocyclic azo compound may be produced by one of the following two basic methods: 1) polymerization of a monomer or an oligomer and 2) polymer reaction of a polymer or an oligomer.

In the case of 1) polymerization, a polymerizable monomer of the following formula (3) having a polymerizable group M is polymerized in the presence of a polymerization initiator such as AIBN, to obtain an oligomer or polymer of the formula (4). An appropriate copolymerizable monomer may be added if necessary to obtain a copolymer having building blocks of the formulae (4) and (5). A copolymer having a number average molecular weight of 1,000 to 1,000,000, preferably 3,000 to 30,000, can be obtained in this manner.

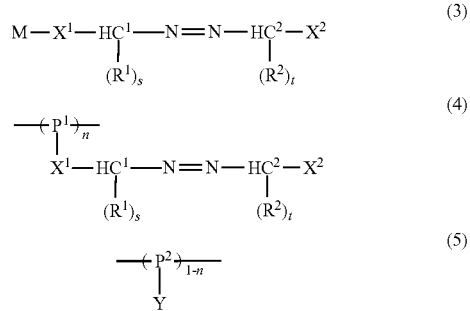

In the formulae (3), (4), and (5), as defined in the formula (1), $HC^1$ and $HC^2$ each represent a ring structure, at least one of them being a heterocyclic structure containing 1 or more heteroatom in the ring, $R^1$ and $R^2$ each represent a hydrogen atom or a substituent connected to the ring structure and may be the same or different ones, and s and t each represent the number thereof. $X^1$ represents a linking group connected to the main chain of the oligomer or polymer, and $X^2$ is a terminal group of a hydrogen atom or a substituent.

M in the formula (3) may be a polycondensation-reactive, polyaddition-reactive, addition-polymerizable, isomerization-polymerizable, or ring opening-polymerizable monomer group.

Further, $P^1$ and $P^2$ in the formulae (4) and (5) each represent a main chain skeleton structure polymerized. n represents a copolymerization composition ratio of the monomer, which is a real number of more than 0 and at most 1.

Y is a side chain, and preferably a liquid crystalline group for efficiently promoting the photo-induced molecular reorientation of the photoresponsive copolymerization component, a functional group having a function of stabilizing the photo-induced molecular reorientation via a hydrogen bond, etc., or an optically high-anisotropic functional group. Examples thereof include groups shown in the following formulae (6), (7), and (8), and groups having 2 azo groups connected, etc. The invention is not limited to the examples.

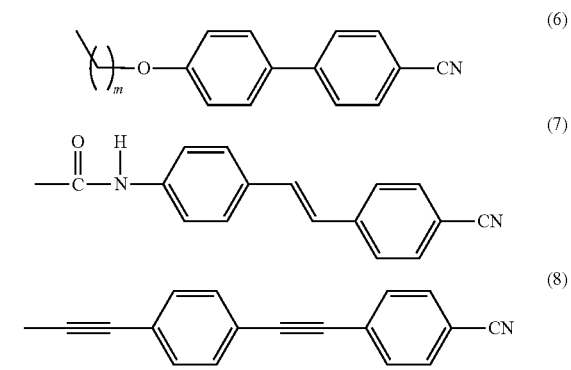

In the case of 2) reaction, for example, a polymerizable monomer represented by the following formula (9) is polymerized in the presence of a polymerization initiator such as AIBN, to obtain an oligomer or polymer of the formula (10). An appropriate copolymerizable monomer of the formula (11) may be added if necessary to obtain a copolymer with building blocks of the formulae (10) and (11) having a number average molecular weight of 300 to 300,000, preferably 1,000 to 30,000. Then, a diazonium ion of the general formula (12) may be interacted to introduce an azo moiety to the aromatic ring $HC^1$ containing the heteroatom via an aromatic electrophilic substitution reaction, to obtain a copolymer with the building blocks of the formulae (4) and (5) having a number average molecular weight of 1,000 to 1,000,000, preferably 3,000 to 30,000.

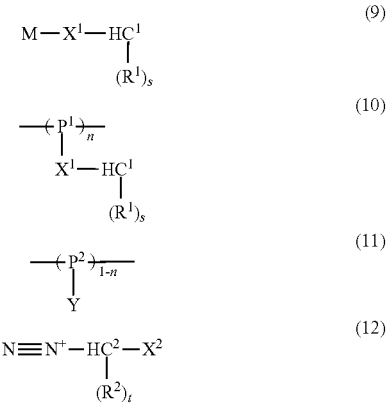

Signs in the formulae are as defined above.

According to the invention, by using the above polymer or oligomer, there is provided the optical information recording material that can record an optical information utilizing change of an optical absorption property or refractive index caused by light irradiation or localized heating, the building block represented by the formula (1) being used as a photoresponsive moiety. For example, the optical information recording material may be used as a rewritable volume hologram memory or a rewritable surface relief memory. The methods of producing and using the material may be selected from various known methods such as spin coating onto a substrate.

The invention will be described in more detail below with reference to Examples.

The invention is not limited to Examples.

EXAMPLES

<A> Synthesis of Methacrylate Copolymer Having Aromatic Heterocycle-Containing Azo Moiety in Side Chain Example 1

4.96 g (30 mmol) of N-hydroxyethyl-N-ethylaniline and 6.27 ml (45 mmol) of triethylamine were dissolved in tetrahydrofuran, and 4.36 ml (40 mmol) of methacryloyl chloride was slowly added thereto dropwise while stirring the mixture in an ice bath. After 3 hours of stirring, the reaction solution was filtered to remove salts, transferred to a separatory funnel, and washed with an aqueous potassium carbonate solution, a saturated sodium chloride solution, and distilled water, and the dichloromethane phase was extracted. The solvent was distilled off under reduced pressure to obtain 15.906 g of Molecule 1 of the following formula as an yellow oil with 83% yield.

Then, 0.274 g (2.06 mmol) of 2-aminoimidazole-4,5-dicarbonitrile was dissolved in 2 M hydrochloric acid, and stirred in an ice bath. Thereto was slowly added a solution prepared by dissolving 0.142 g (2.06 mmol) of sodium nitrite in distilled water dropwise. To this was slowly added a solution of 10.4 g (1.71 mmol) of Molecule 1 dissolved in a 4 N aqueous sodium hydroxide solution dropwise, stirred at 0° C. for 2 hours and at the room temperature for 3 hours, and filtered to obtain red precipitates. Further, the precipitates were subjected to recrystallization from u-hexane, to obtain 20.43 g of Molecule 2 of the following formula having an azo group sandwiched between 4,5-dicyanoimidazole and N-ethylaniline with a yield of 55%. The $^1$H-NMR data of the obtained molecule were as shown in Table 1, and the IR spectrum thereof was as shown in FIG. 1.

TABLE 1

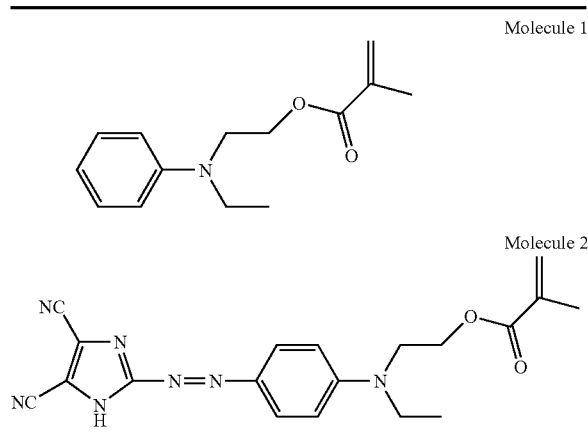

Molecule 1

Molecule 2

Molecule (2) $^1$H NMR Data: $^1$HNMR (δ[ppm], acetone-d$_6$): 1.29 (t, 3H), 1.93 (s, 3H), 3.62 (q, 2H), 3.78 (t, 2H), 4.39 (t, 2H), 5.60 (t, 1H), 6.10 (t, 1H), 6.81 (d, 2H), 7.83 (d, 2H).

0.344 g (3.42 mmol) of methyl methacrylate, 20.8 g (3.42 mmol) of Molecule 2, and 0.045 g (0.27 mmol) of 2,2'-azobisisobutyronitrile were dissolved in 35 ml of tetrahydrofuran. The resultant solution was added to a 150-ml flask and subjected to deaeration using liquid nitrogen, the reaction system was sealed, and polymerization was carried out at 65° C. After 24 hours, the polymerization product was isolated and purified by repeating reprecipitation in methanol twice.

Figure 2:
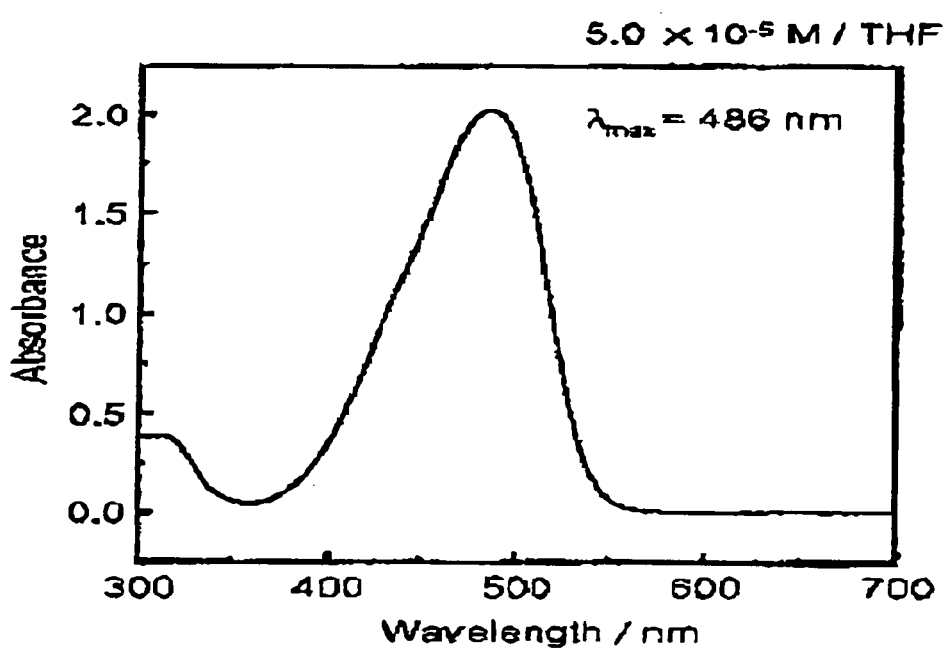
FIG. 2 is the absorption spectrum of the random copolymer of Example 1.

As a result, a 1:1 random copolymer of methyl methacrylate and Molecule 2 represented by the following formula was obtained as red powder with a number average molecular weight of 12,000. The glass transition temperature of the obtained copolymer determined by DSC analysis was 175° C., and the absorption spectrum thereof (5×10$^{-5}$ mol/L in THF) was as shown in FIG. 2.

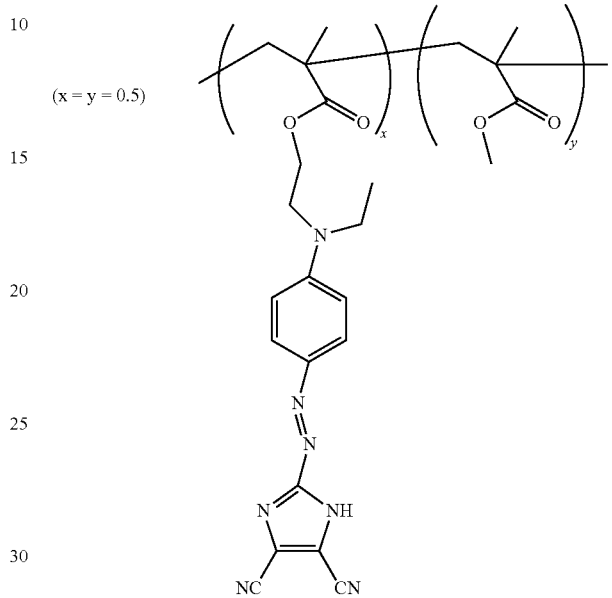

(x = y = 0.5)

Example 2

Molecule 1 was synthesized in the same manner as Example 1. 0.429 g (4.29 mmol) of methyl methacrylate, 1.0 g (4.29 mmol) of Molecule 1, and 0.028 g (0.172 mmol) of 2,2'-azobisisobutyronitrile were dissolved in 40 ml of tetrahydrofuran. The resultant solution was added to a 150-ml flask and subjected to deaeration using liquid nitrogen, the reaction system was sealed, and polymerization was carried out at 65° C. After 24 hours, the polymerization product was isolated and purified by repeating reprecipitation in methanol twice. As a result, 0.83 g of a 1:1 copolymer of methyl methacrylate and Molecule 1 was obtained as white powder with a yield of 58%.

Then, 0.05 g (0.376 mmol) of 2-aminoimidazole-4,5-dicarbonitrile was dissolved in 2 M hydrochloric acid, and stirred in an ice bath. Thereto was slowly added a solution prepared by dissolving 0.026 g (0.376 mmol) of sodium sulfite in distilled water dropwise. To this was slowly added an acetic acid solution of 0.055 g (0.25 mmol, based on the unit average molecular weight) of the 1:1 random copolymer of methyl methacrylate and Molecule 1 of N-methacryloyloxyethyl-N-ethylaniline dropwise, stirred at 0° C. for 2 hours and at the room temperature for 3 hours, and filtered to obtain red precipitates. Further, the precipitates were purified by reprecipitation in methanol, to obtain 0.013 g of a random copolymer of methyl methacrylate and Molecule 2 as red powder with a copolymerization ratio of 1:1 (x=y=0.5). The glass transition temperature and the absorption spectrum of the obtained copolymer were the same as the case of Example 1.

Example 3

Molecule 1 was synthesized in the same manner as Example 1. 0.161 g (1.61 mmol) of methyl methacrylate, 1.5 g (6.43 mmol) of Molecule 1, and 0.053 g (0.322 mmol) of 2,2'-azobisisobutyronitrile were dissolved in 40 ml of tetrahydrofuran. The resultant solution was added to a 150-ml flask and subjected to deaeration using liquid nitrogen, the reaction system was sealed, and polymerization was carried out at 65° C. After 24 hours, the polymerization product was isolated and purified by repeating reprecipitation in methanol twice. As a result, 1.05 g of a 1:4 random copolymer of methyl methacrylate and Molecule 1 was obtained as white powder with a yield of 63%.

Then, 0.048 g (0.36 mmol) of 2-aminoimidazole-4,5-dicarbonitrile was dissolved in 2 M hydrochloric acid, and stirred in an ice bath. Thereto was slowly added a solution prepared by dissolving 0.025 g (0.36 mmol) of sodium sulfite in distilled water dropwise. To this was slowly added an acetic acid solution of 0.05 g (0.24 mmol, based on the unit average molecular weight) of the 1:4 random copolymer of methyl methacrylate and Molecule 1 dropwise, stirred at 0° C. for 2 hours and at the room temperature for 3 hours, and filtered to obtain red precipitates Further, the precipitates were purified by reprecipitation in methanol, to obtain 0.062 g of a random copolymer of methyl methacrylate and Molecule 2 as red powder with a copolymerization ratio of 1:4 ($x=0.2$, $y=0.8$) with a yield of 53%.

Example 4

Molecule 1 was synthesized in the same manner as Example 1. 1.03 g (10 mmol) of methyl methacrylate, 0.6 g (257 mmol) of Molecule 1 of N-methacryloyl oxyethyl-N-ethylaniline, and 0.053 g (0.50 mmol) of 2,2'-azobisisobutyronitrile were dissolved in 60 ml of tetrahydrofuran. The resultant solution was added to a 150-ml flask and subjected to deaeration using liquid nitrogen, the reaction system was sealed, and polymerization was carried out at 65° C. After 24 hours, the polymerization product was isolated and purified by repeating reprecipitation in methanol twice. As a result, 1.1 g of a 4:1 random copolymer of methyl methacrylate and Molecule 1 was obtained as white powder with a yield of 69%.

Then, 0.079 g (0.59 mmol) of 2-aminoimidazole-4,5-dicarbonitrile was dissolved in 2 M hydrochloric acid, and stirred in an ice bath. Thereto was slowly added a solution prepared by dissolving 0.041 g (0.59 mmol) of sodium nitrite in distilled water dropwise. To this was slowly added an acetic acid solution of 0.05 g (0.39 mmol, based on the unit average molecular weight) of the 4:1 copolymer of methyl methacrylate and Molecule 1 dropwise, stirred at 0° C. for 2 hours and at the room temperature for 3 hours, and filtered to obtain red precipitates. Further, the precipitates were purified by reprecipitation in methanol, to obtain 0.021 g of a random copolymer of methyl methacrylate and Molecule 2 as red powder with a copolymerization ratio of 4:1 ($x=0.8$, $y=0.2$) with a yield of 35%

Example 5

1.23 g (10 mmol) of 4-aminobenzyl alcohol was dissolved in 2 M hydrochloric acid, and stirred in an ice bath. Thereto was slowly added a solution prepared by dissolving 0.69 g (10 mmol) of sodium nitrite in a small amount of distilled water dropwise. The mixture was stirred for about 30 minutes, 0.921 g (10 mmol) of 2-cyanopyrrole dissolved in a 1 M aqueous sodium hydroxide solution was slowly added dropwise, and the resultant was stirred for about 5 hours. The mixture was filtrated after completion of the reaction, and the obtained orange-yellow powder washed with water twice and subjected to recrystallization from a water/ethanol mixed solvent, to obtain 0.191 g of Molecule 3 of the following formula as orange powder with a yield of 8.4%.

0.1 g (0.44 mmol) of Molecule 3 dissolved in chloroform and 0.049 g (0.49 mmol) of triethylamine were stirred in an ice bath, and 0.051 g (0.49 mmol) of methacryloyl chloride was slowly added thereto dropwise and stirred overnight. After completion of the reaction, the resultant mixture washed with an aqueous potassium carbonate solution, a saturated sodium chloride solution, and distilled water, and extracted with chloroform. The solvent was distilled off under reduced pressure, to obtain orange powder of Molecule 4 of the following formula having an azo group sandwiched between 2-cyanopyrrole and benzyl ester.

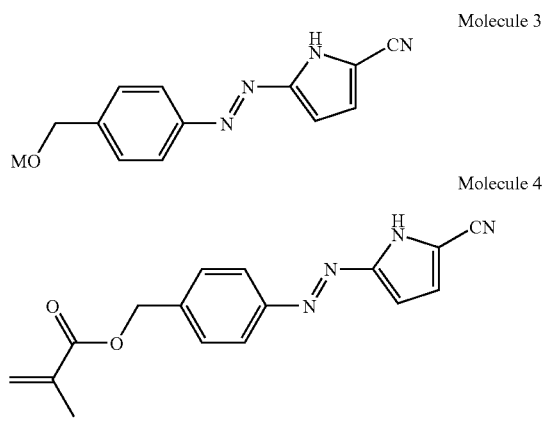

A desired random copolymer of thus synthesized Molecule 4 and methyl methacrylate was produced in the same manner as Examples 1 to 4, and the obtained copolymer had a number average molecular weight of 8,000.

The following formula shows the structure of the copolymer.

($x = y = 0.5$)
($x = 0.2$, $y = 0.8$)
($x = 0.8$, $y = 0.2$)

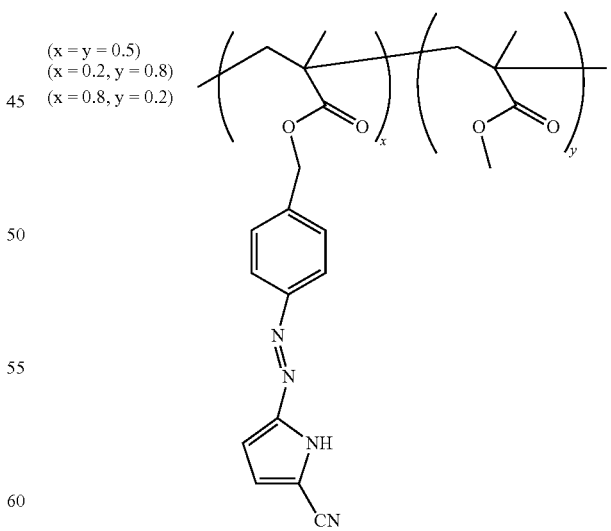

Example 6

0.238 g (2 mmol) of 5-amino-2-cyanopyridine was dissolved in 2 M hydrochloric acid, and stirred in an ice bath.

Thereto was slowly added a solution prepared by dissolving 0.16 g (2.3 mmol) of sodium nitrite in a small amount of distilled water dropwise. The mixture was stirred for about 30 minutes, thereto was added 0.4 g (10 mmol) of sodium hydroxide, and a solution prepared by dissolving 0.33 g (2 mmol) of N-hydroxyethyl-N-ethylaniline in 40 ml of distilled water and 40 ml of methanol was slowly added dropwise and stirred. The mixture was filtrated after completion of the reaction, and the obtained red powder washed with water twice and subjected to recrystallization from a water/ethanol mixed solvent, to obtain Molecule 5 of the following formula as red powder.

0.1 g (0.34 mmol) of Molecule 5 dissolved in chloroform and 0.038 g (0.38 mmol) of triethylamine were stirred in an ice bath, and 0.040 g (0.38 mmol) of methacryloyl chloride was slowly added thereto dropwise and stirred overnight. After completion of the reaction, the resultant mixture washed with an aqueous potassium carbonate solution, a saturated sodium chloride solution, and distilled water, and extracted with chloroform. The solvent was distilled off under reduced pressure, to obtain red powder of Molecule 6 of the following formula having an azo group sandwiched between 2-cyanopyridine and N-ethylaniline. The $^1$H-NMR data and elementary analysis values of the obtained molecule were as shown in Table 2.

TABLE 2

Molecule 5

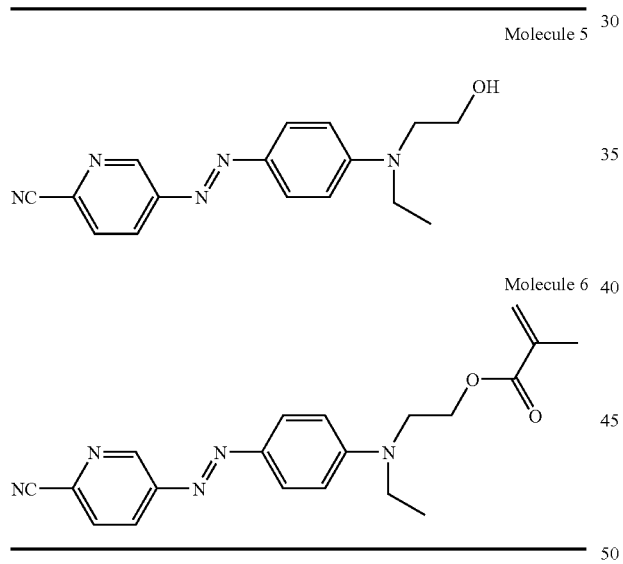

Molecule 6

Molecule (6) $^1$H NMR Data: $^1$H-NMR, δ (ppm): 1.27 (t, 3H), 1.97 (s, 3H), 3.56 (m, 2H), 3.74 (t, 2H), 4.38 (t, 2H), 5.61 (d, 1H), 6.16 (d, 1H), 7.05 (d, 2H), 7.82 (d, 1H), 7.98 (d, 2H), 8.19 (d, 1H), 9.2 (s, 1H).
Chemical Element Analysis Data: Calcd. for $C_{20}H_{21}N_6$: C 66.10%, H 5.82%, N 19.27%.
Found: C 65.57% H 5.63% N 19.11%

A desired random copolymer of thus synthesized Molecule 6 and methyl methacrylate was produced in the same manner as Examples 1 to 4, and the obtained copolymer had a number average molecular weight of 16,000.

Figure 3:
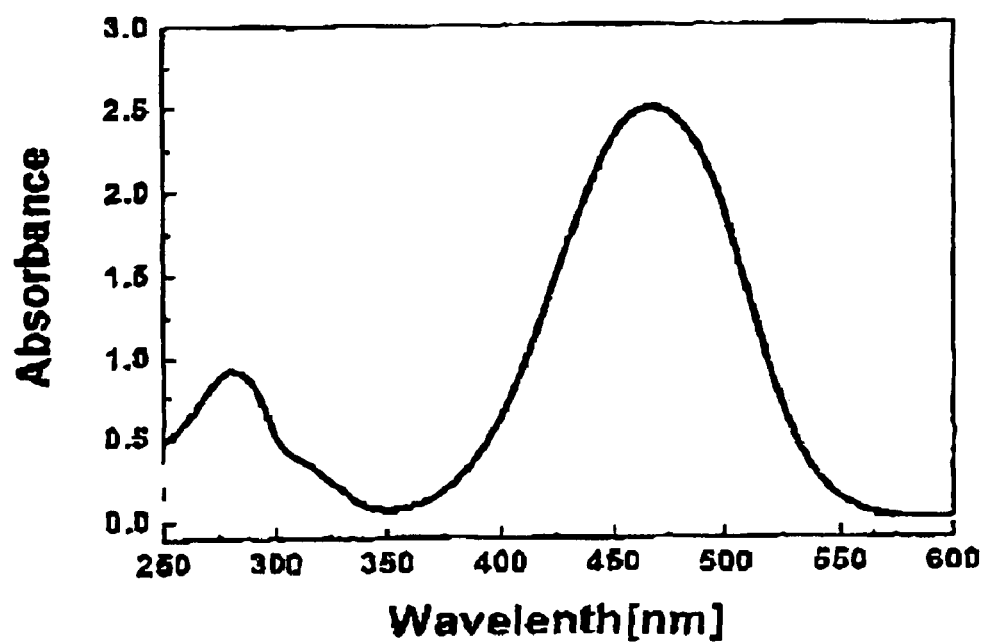
FIG. 3 is the absorption spectrum of the random copolymer of Example 6.

The following formula shows the structure of the copolymer. The glass transition temperature of the obtained copolymer determined by DSC analysis was 125° C., and the absorption spectrum thereof ($1 \times 10^{-4}$ mol/L in $CHCl_3$) was as shown in FIG. 3.

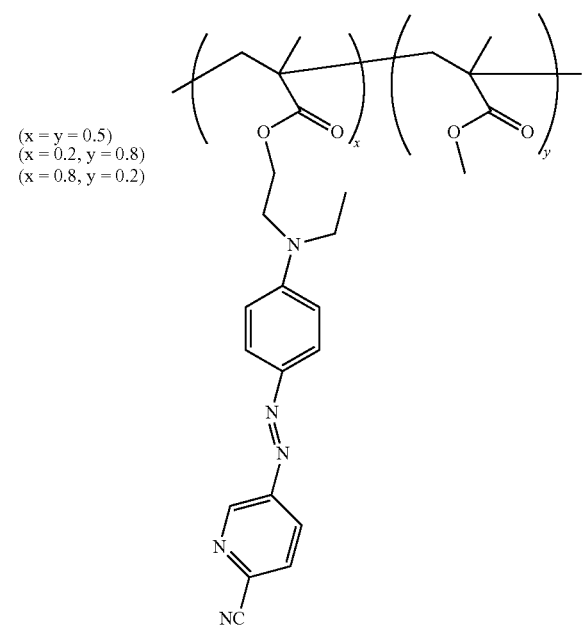

(x = y = 0.5)
(x = 0.2, y = 0.8)
(x = 0.8, y = 0.2)

Example 7

In the same manner as Example 6, a molecular compound of the following formula having a similar structure to that of the above Molecule 6 was obtained.

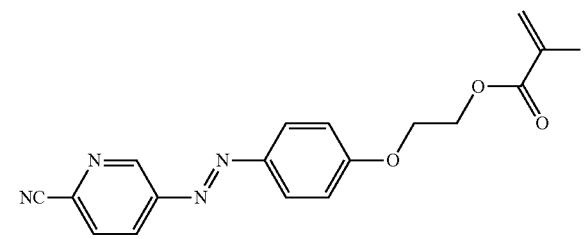

The $^1$H-NMR data of the obtained molecule were as shown in Table 3.

TABLE 3

$^1$H NMR Data: $^1$H-NMR, δ (ppm): 1.97 (s, 3H), 4.34 (t, 2H), 4.58 (t, 2H),
5.61 (d, 1H), 6.16 (d, 1H), 7.05 (d, 2H), 7.82 (d, 1H), 7.98 (d, 2H),
8.19 (d, 1H), 9.2 (s, 1H). Calcd. for $C_{18}H_{16}N_4$;
C 64.28%, H 4.79%, N 16.66%. Found; C 63.87% H 4.78% N 16.54%
(Chemical Element Analysis Data)

Figure 4:
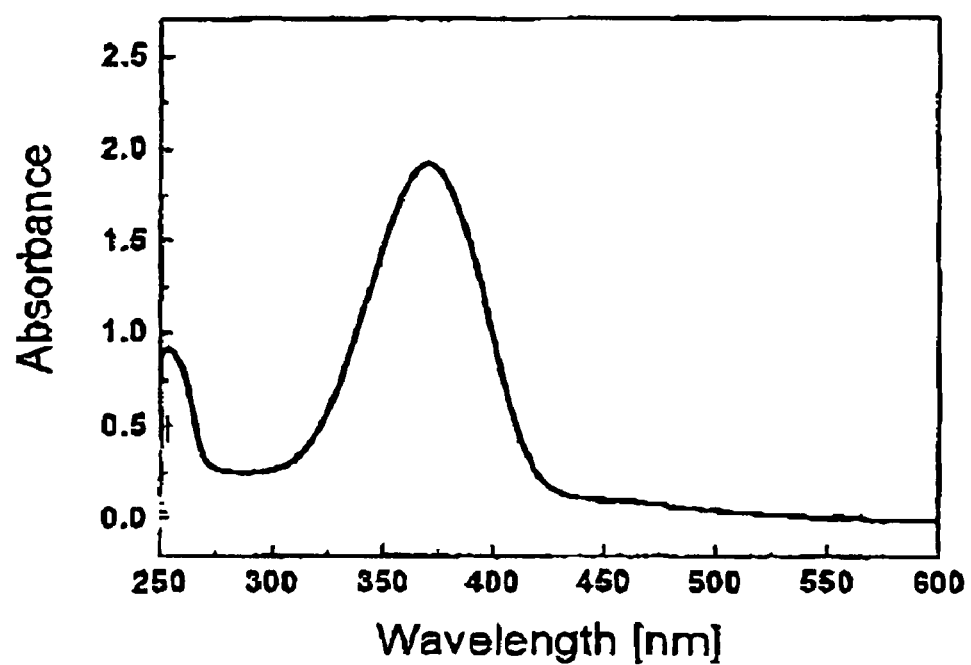
FIG. 4 is the absorption spectrum of the random copolymer of Example 7.

Further, a random copolymer of this molecular compound and methyl methacrylate was obtained. The obtained copolymer had the structure represented by the following formula and the absorption spectrum thereof was as shown in FIG. 4.

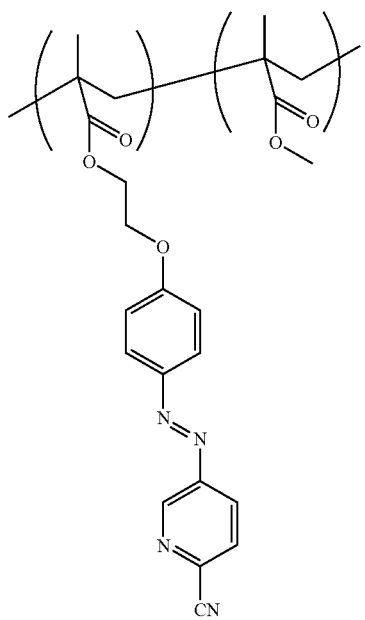

Example 8

1.08 g (10 mmol) of 2-methylaminopyridine, 1.6 g (20 mmol) of 2-chloroethanol, 3.32 g (20 mmol) of potassium iodide, and 2.76 g (20 mmol) of potassium carbonate were dissolved in 100 ml of dimethylformamide, and reacted at 120° C. for 2 hours. Then, the reaction mixture was stirred at the room temperature for 48 hours, thereto were added a 10% aqueous sodium hydroxide solution and distilled water in the appropriate amounts, to obtain precipitates. The precipitates were isolated by filtration, and the obtained crystal washed with water twice to obtain N-hydroxyethyl-N-methylaminopyridine.

0.238 g (2 mmol) of 5-amino-2-cyanopyridine was dissolved in 2 M hydrochloric acid, and stirred in an ice bath. Thereto was slowly added a solution prepared by dissolving 0.16 g (2.3 mmol) of sodium nitrite in a small amount of distilled water dropwise. The mixture was stirred for about 30 minutes, thereto was added 0.4 g (10 mmol) of sodium hydroxide, and a solution prepared by dissolving 0.304 g (2 mmol) of N-hydroxyethyl-N-methylaminopyridine in 40 ml of distilled water and 40 ml of methanol was slowly added dropwise and stirred. The mixture was filtrated after completion of the reaction, and the obtained red powder washed with water twice and subjected to recrystallization from a water/ethanol mixed solvent, to obtain a red crystal of Molecule 7 of the following formula having an azo group sandwiched between 2-cyanopyridine and N-methylaminopyridine.

0.1 g (0.35 mmol) of Molecule 7 dissolved in chloroform and 0.039 g (0.39 mmol) of triethylamine were stirred in an ice bath, aid 0.041 g (0.39 mmol) of methacryloyl chloride was slowly added thereto dropwise and stirred overnight. After completion of the reaction, the resultant mixture washed with an aqueous potassium carbonate solution, a saturated sodium chloride solution, and distilled water, and extracted with chloroform. The solvent was distilled off under reduced pressure, to obtain red powder of Molecule 8 of the following formula.

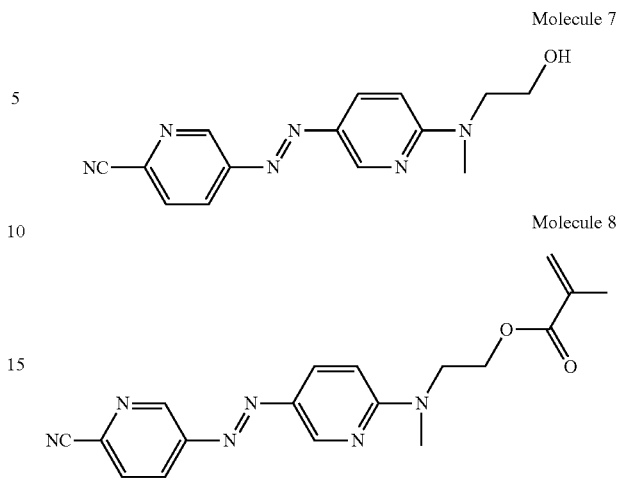

A desired random copolymer of Molecule 8 and methyl methacrylate was produced in the same manner as Examples 1 to 4, and the obtained copolymer had a number average molecular weight of 7,000.

The following formula shows the structure of the copolymer.

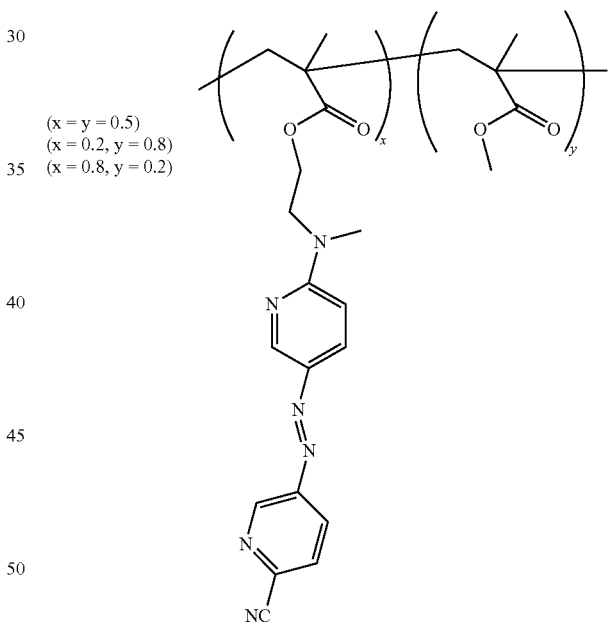

(x = y = 0.5)
(x = 0.2, y = 0.8)
(x = 0.8, y = 0.2)

<B> Synthesis of Compound Having Azo Group Sandwiched Between Heterocycles

In Examples 8 to 15, synthesis examples of compounds with an azo group sandwiched between heterocycles are described. The synthesized compounds are converted to monomers having a methacrylo group, and copolymerized with eg. methyl methacrylate to produce random copolymers in the same manner as Examples 1 to 7.

Example 9

0338 g (2 mmol) of 2-amino-5-trifluoromethyl-1,3,4-thiadiazole was dissolved in 2 M hydrochloric acid, and stirred in an ice bath. Thereto was slowly added a solution prepared by dissolving 0.16 g (2.3 mmol) of sodium nitrite in a small amount of distilled water dropwise. The mixture was stirred for about 30 minutes, thereto was added 0.4 g (10 mmol) of sodium hydroxide, and a solution prepared by dissolving 0.304 g (2 mmol) of N-hydroxyethyl-N-methylaminopyridine in 40 ml of distilled water and 40 ml of methanol was slowly added dropwise and stirred. The mixture was filtrated after completion of the reaction, and the obtained red powder washed with water twice and subjected to recrystallization from a water/ethanol mixed solvent, to obtain a red crystal of a compound having an azo group sandwiched between 5-trifluoromethylthiadiazole and N-methylaminopyridine. Then, in the same manner as Examples 1 to 8, the obtained compound was reacted with methacryloyl chloride and converted to a monomer connected to a methacryloyl group. The monomer compound has the structure represented by the following formula.

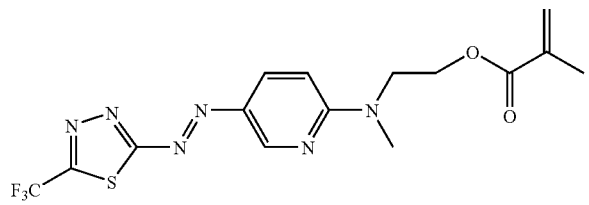

Example 10

0.20 g (2 mmol) of 2-aminothiazole was dissolved in 2 M hydrochloric acid, and stirred in an ice bath. Thereto was slowly added a solution prepared by dissolving 0.16 g (2.3 mmol) of sodium nitrite in a small amount of distilled water dropwise. The mixture was stirred for about 30 minutes, thereto was added 0.4 g (10 mmol) of sodium hydroxide, and a solution prepared by dissolving 0304 g (2 mmol) of N-hydroxyethyl-N-methylaminopyridine in 40 ml of distilled water and 40 ml of methanol was slowly added dropwise and stirred. The mixture was filtrated after completion of the reaction, and the obtained orange powder washed with water twice and subjected to recrystallization from a water/ethanol mixed solvent, to obtain an orange crystal of a compound having an azo group sandwiched between thiazole and N-methylaminopyridine. Then, in the same manner as Examples 1 to 8, the obtained compound was reacted with methacryloyl chloride and converted to a monomer connected to a methacryloyl group. The monomer compound has the structure represented by the following formula

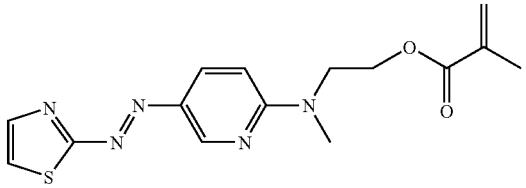

Example 11

58.7 mg (0.58 mmol) of 2-aminothiazole was dissolved in 2 M hydrochloric acid, and stirred in an ice bath. Thereto was slowly added a solution prepared by dissolving 80.5 mg (0.12 mmol) of sodium nitrite in a small amount of distilled water dropwise. After the mixture was stirred for about 15 minutes, an aqueous solution containing 0.612 g of phenol was slowly added dropwise thereto and stirred. After completion of the reaction, the resultant solution was adjusted to about pH 7 and subjected to extraction using methylene chloride. The solvent was removed from the resultant solution to obtain a crude product. The obtained crude product was purified using a silica gel column to obtain a molecule of the following formula as a red solid.

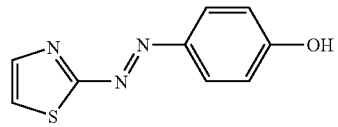

The mass spectrum data of the obtained molecule were as shown in Table 4.

TABLE 4

Mass (EI⁺, 70 eV) m/z (rel intensity) = 205 ($M^+$. 36).
177 ($M^+$−28. 100), 149 ($M^+$−56. 28). 121 ($M^+$−thiazole,
21), 93 ($C_6H_4$—OH. 71)

Example 12

0.168 g (2 mmol) of 3-amino-1,2,4-triazole was dissolved in 2 M hydrochloric acid, and stirred in an ice bath. Thereto was slowly added a solution prepared by dissolving 0.16 g (2.3 mmol) of sodium nitrite in a small amount of distilled water dropwise. The mixture was stirred for about 30 minutes, thereto was added 0.4 g (10 mmol) of sodium hydroxide, and a solution prepared by dissolving 0.304 g (2 mmol) of N-hydroxyethyl-N-methylaminopyridine in 40 ml of distilled water and 40 ml of methanol was slowly added dropwise and stirred. The mixture was filtrated after completion of the reaction, and the obtained red powder washed with water twice and subjected to recrystallization from a water/ethanol mixed solvent, to obtain a red crystal of a compound having an azo group sandwiched between triazole and N-methylaminopyridine. Then, in the same manner as Examples 1 to 8, the obtained compound was reacted with methacryloyl chloride and converted to a monomer connected to a methacryloyl group. The monomer compound has the structure represented by the following formula.

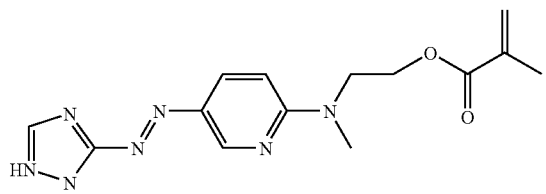

Example 13

0.192 g (2 mmol) of 2-amino-1,2,4-triazine was dissolved in 2 M hydrochloric acid, and stirred in an ice bath. Thereto was slowly added a solution prepared by dissolving 0.16 g (2.3 mmol) of sodium nitrite in a small amount of distilled water dropwise. The mixture was stirred for about 30 minutes, thereto was added 0.4 g (10 mmol) of sodium hydroxide, and a solution prepared by dissolving 0304 g (2 mmol) of N-hydroxyethyl-N-methylaminopyridine in 40 ml of distilled water and 40 ml of methanol was slowly added dropwise and stirred. The mixture was filtrated after completion of the reaction, and the obtained red powder washed with water twice and subjected to recrystallization from a water/ethanol mixed solvent, to obtain a red crystal of a compound having an azo group sandwiched between triazine and N-methylaminopyridine. Then, in the same manner as Examples 1 to 8, the obtained compound was reacted with methacryloyl chloride and converted to a monomer connected to a methacryloyl group. The monomer compound has the structure represented by the following formula.

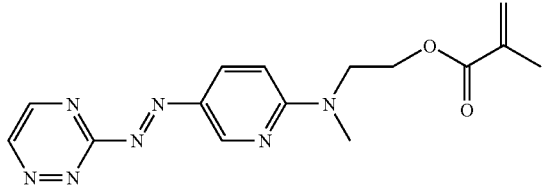

Example 14

0.166 g (2 mmol) of 2-amino-oxazole was dissolved in 2 M hydrochloric acid, and stirred in an ice bath. Thereto was slowly added a solution prepared by dissolving 0.16 g (23 mmol) of sodium nitrite in a small amount of distilled water dropwise. The mixture was stirred for about 30 minutes, thereto was added 0.4 g (10 mmol) of sodium hydroxide, and a solution prepared by dissolving 0.304 g (2 mmol) of N-hydroxyethyl-N-methylaminopyridine in 40 ml of distilled water and 40 ml of methanol was slowly added dropwise and stirred. The mixture was filtrated after completion of the reaction, and the obtained red powder washed with water twice and subjected to recrystallization from a water/ethanol mixed solvent, to obtain a red crystal of a compound having an azo group sandwiched between oxazole and N-methylaminopyridine. Then, in the same manner as Examples 1 to 8, the obtained compound was reacted with methacryloyl chloride and converted to a monomer connected to a methacryloyl group. The monomer compound has the structure represented by the following formula.

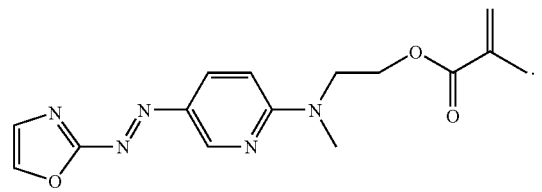

Example 15

0.168 g (2 mmol) of 2-aminoimidazole was dissolved in 2 M hydrochloric acid, and stirred in an ice bath. Thereto was slowly added a solution prepared by dissolving 0.16 g (23 mmol) of sodium nitrite in a small amount of distilled water dropwise. The mixture was stirred for about 30 minutes, thereto was added 0.4 g (10 mmol) of sodium hydroxide, and a solution prepared by dissolving 0.304 g (2 mmol) of N-hy-droxyethyl-N-methylaminopyridine in 40 ml of distilled water and 40 ml of methanol was slowly added dropwise and stirred. The mixture was filtrated after completion of the reaction, and the obtained red powder washed with water twice and subjected to recrystallization from a water/ethanol mixed solvent, to obtain a red crystal of a compound having an azo group sandwiched between imidazole and N-methylaminopyridine. Then, in the same manner as Examples 1 to 8, the obtained compound was reacted with methacryloyl chloride and converted to a monomer connected to a methacryloyl group. The monomer compound has the structure represented by the following formula.

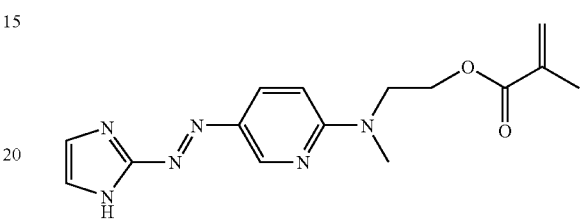

Example 16

1.20 g (10.1 mmol) of S-amino-2-cyanopyridine was dissolved in 2 M hydrochloric acid, and stirred in an ice bath. Thereto was slowly added a solution prepared by dissolving 0.70 g (10.2 mmol) of sodium nitrite in a small amount of distilled water dropwise. The mixture was stirred for about 30 minutes, and was slowly added dropwise to a solution prepared by dissolving 0.60 g (5.99 mmol) of 2(5H)thiophene in 20 ml of a 10% aqueous potassium hydroxide solution, and stirred. After completion of the reaction, 2 M hydrochloric acid was added to the resultant solution until the pH thereof reached about 4. The mixture was filtrated to obtain a crude product. The mixture was separated and purified using a silica gel column to obtain 0.20 g of an ocherous solid.

0.12 g (0.35 mmol) of the obtained molecule dissolved in chloroform and 0.039 g (0.39 mmol) of triethylamine were stirred in an ice bath, and 0.041 g (0.38 mmol) of methacryloyl chloride was slowly added dropwise thereto and stirred overnight. After completion of the reaction, the resultant mixture washed with an aqueous potassium carbonate solution, a saturated sodium chloride solution, and distilled water, and extracted with chloroform. The solvent was distilled off under reduced pressure, to obtain a molecule of the following formula as ocherous powder.

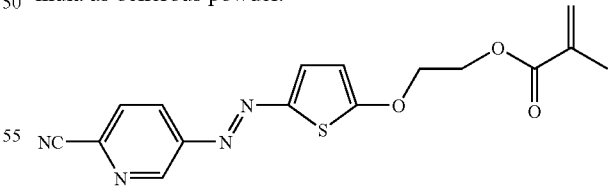

The $^1$H-NMR data of the obtained molecule were as shown in Table 5.

TABLE 5

$^1$H NMR Data: $^1$H-NMR in Acetone-D6, δ (ppm): 1.97 (s, 3H), 4.34 (t, 2H), 4.58 (t, 2H), 5.61 (d, 1H), 6.16 (d, 1H), 6.67 (d, 1H), 7.84 (d, 1H), 7.99 (d, 2H), 8.65 (d, 2H), 10.21 (s, 1H)

Example 17

1.18 g (10.0 mmol) of 4-cyanoaniline was dissolved in 2 M hydrochloric acid, and stirred in an ice bath. Thereto was slowly added a solution prepared by dissolving 0.70 g (10.2 mmol) of sodium nitrite in a small amount of distilled water dropwise. The mixture was stirred for about 30 minutes, and was slowly added dropwise to a solution prepared by dissolving 0.60 g (6.00 mmol) of 2(5H)thiophene in 20 ml of a 10% aqueous potassium hydroxide solution, and stirred. After completion of the reaction, 2 M hydrochloric acid was added to the resultant solution until the pH thereof reached about 4. The mixture was filtrated to obtain a crude product. The mixture was separated and purified using a silica gel column to obtain 0.29 g of an ocherous solid.

0.12 g (0.35 mmol) of the obtained molecule dissolved in chloroform and 0.039 g (0.39 mmol) of triethylamine were stirred in an ice bath, and 0.041 g (0.39 mmol) of methacryloyl chloride was slowly added dropwise thereto and stirred overnight. After completion of the reaction, the resultant mixture washed with an aqueous potassium carbonate solution, a saturated sodium chloride solution, and distilled water, and extracted with chloroform. The solvent was distilled off under reduced pressure, to obtain a molecule of the following formula as ocherous powder.

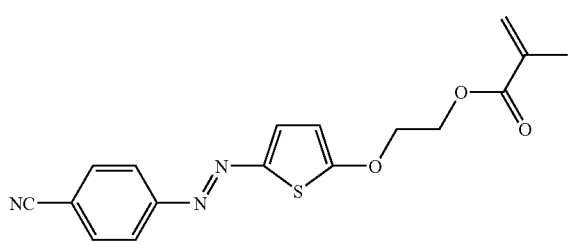

The $^1$H-NMR data of the obtained molecule were as shown in Table 6.

TABLE 6

$^1$H NMR Data: $^1$H-NMR. δ(ppm): 1.97 (s, 3H). 4.34 (t, 2H), 4.58 (t, 2H),
5.61 (d, 1H), 6.16 (d, 1H), 6.52 (d, 1H), 7.23d, 2H), 7.62 (d, 2H), 7.73 (d, 1H)

Example 18

In the same manner as Example 10, a compound represented by the following formula having an azo group sandwiched between cyanopyridine and N-methylaminopyridine or N-methylamino-methylpyridine was obtained.

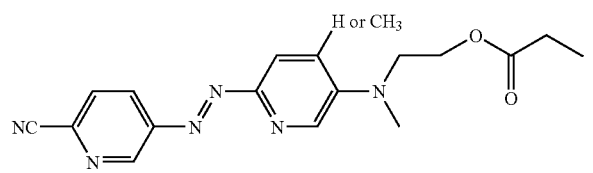

Example 19

In the same manner as Example 11, 52.2 mg (0.57 mmol) of 3-aminopyridine was dissolved in 2 M hydrochloric acid, and stirred in an ice bath. Thereto was slowly added a solution prepared by dissolving 78.2 mg (0.11 mmol) of sodium nitrite in a small amount of distilled water dropwise. After the mixture was stirred for about 15 minutes, an aqueous solution containing 0.608 g of phenol was slowly added dropwise thereto and stirred. After completion of the reaction, the resulting solution was adjusted to about pH 7 and subjected to extraction using methylene chloride. The solvent was removed from the resultant solution to obtain a crude product. The obtained crude product was purified using a silica gel column to obtain 28.4 mg of a molecule represented by the following formula as an orange solid.

The mass spectrum data of the obtained molecule were as shown in Table 7.

TABLE 7

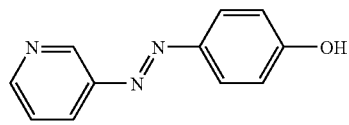

Mass (EI$^+$, 70 eV) m/z (rel intensity) = 199 (M$^+$, 100), 121 (M$^+$-pyridine, 49), 93 (C$_6$H$_4$—OH, 81)

<C> Evaluation of Photo-Induced Birefringence Property

Example 20

Comparison Between Cyanoazobenzene and Dicyanoimidazole

Polymers 1 and 2 of the following formulae were compared with respect to properties.

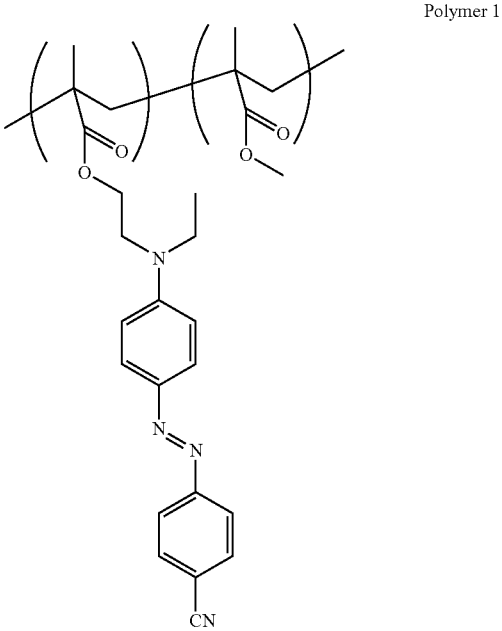

Polymer 1

Polymer 2

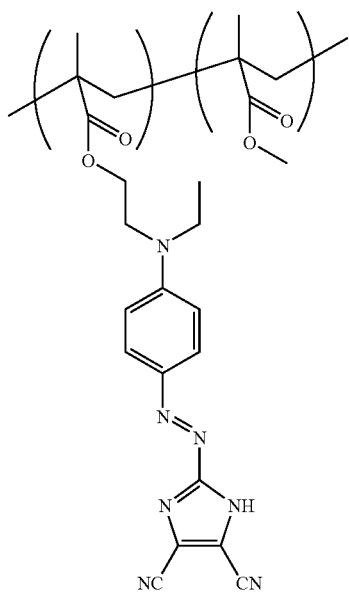

Figure 5:
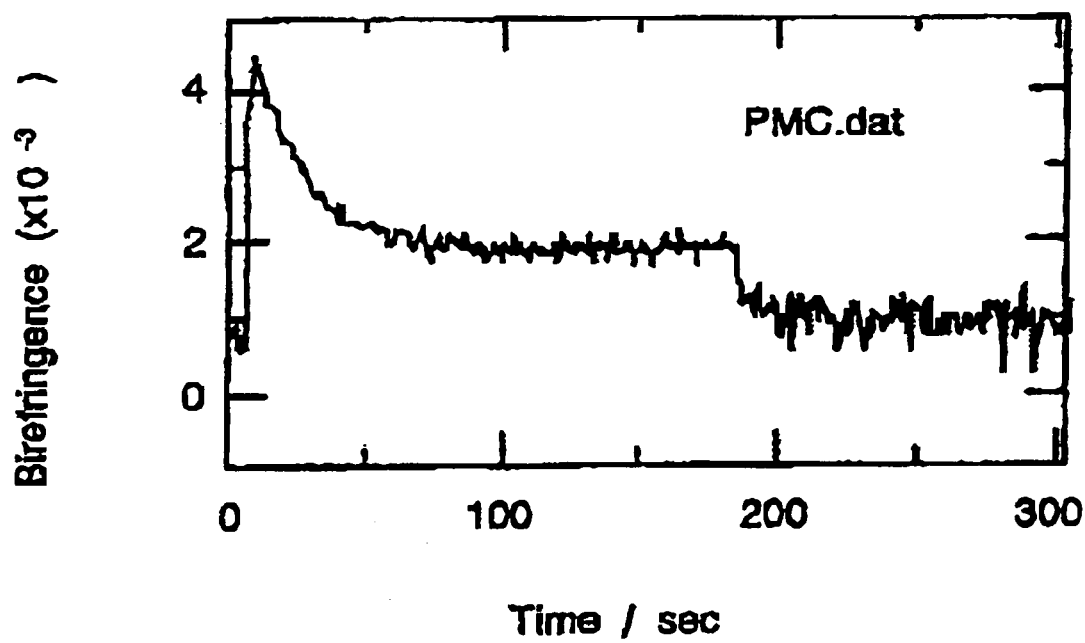
FIG. 5 is a diagram showing the photo-induced birefringence change of Polymer 1 of Example 20 as a comparative example with time after exciting light irradiation.
Figure 6:
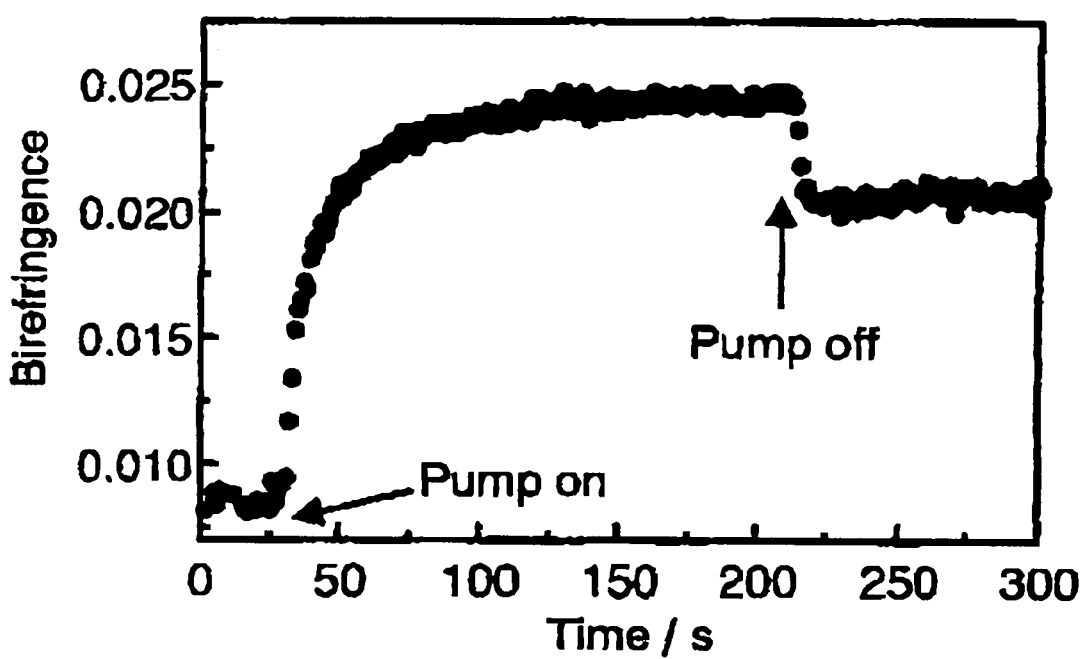
FIG. 6 is a diagram showing the photo-induced birefringence change of Polymer 2 of Example 20 with time after exciting light irradiation.
Figure 7:
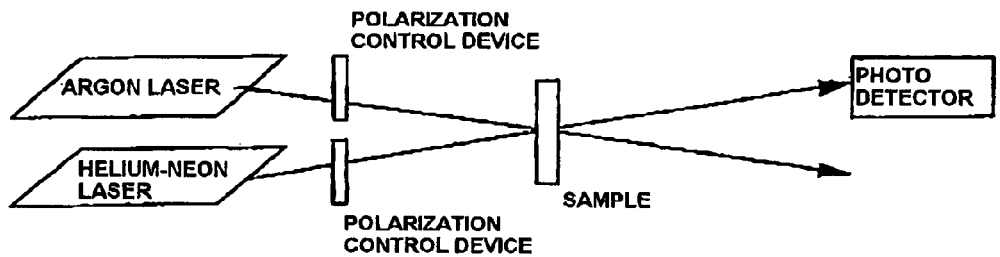
FIG. 7 is a view showing the structure of an optical system for measuring photo-induced birefringence.

FIGS. 5 and 6 each show photo-induced birefringence dynamics of Polymers 1 and 2, measured by an optical system of FIG. 7. A linearly polarized light of 488 nm and 1 W/cm$^2$ from an argon ion laser was used as an exciting light, and a linearly polarized light of 633 nm and 30 mW/cm$^2$ from helium ion was used as a probe light. The exciting light was designed to be capable of exciting a sufficiently wider range as compared to the probe light. The exciting light was irradiated within the range of 10 to 180 seconds of the transverses of the diagrams.

Each sample was obtained by spin-coating a 1-mm-thick glass substrate with a chloroform-tetrahydrofuran solution of each Polymer (10 wt %) at 700 revolutions/minute. As shown in FIG. 1, Polymer 1 made a remarkable response immediately after the exciting light irradiation and then was rapidly relaxed, so that the photo-induced birefringence value was stabilized at a constant value. Further, it was found that, when the exciting light irradiation was stopped, the photo-induced birefringence value was reduced by about 50%. On the contrary, as shown in FIG. 2, the novel compound Polymer 2 did not show the rapid increase and decrease immediately after the exciting light irradiation unlike Polymer 1, and made a stable and rapid response. Further, it was confirmed that the photo-induced birefringence value of Polymer 2 was reduced advantageously only by about 25% after stopping the exciting light irradiation, ½ of the reduction of Polymer 1. Furthermore, the absolute value thereof was 0.018, which was 20 times as large as that of Polymer 1, and thus it was clear that Polymer 2 could act as an optical memory material with excellent properties of the large photo-induced birefringence value and small relaxation.

Example 21

In the same manner as Example 20, the homopolymer of the invention represented by the following formula and the homopolymer of cyanoazobenzene were compared and evaluated with respect to photoresponsive properties.

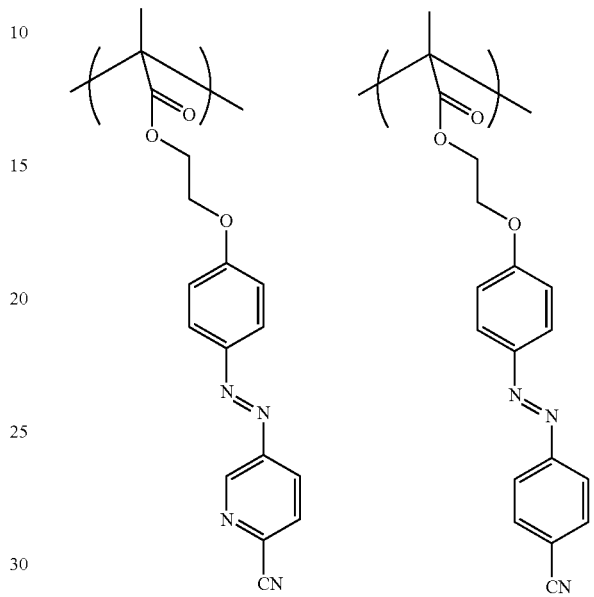

Figure 8:
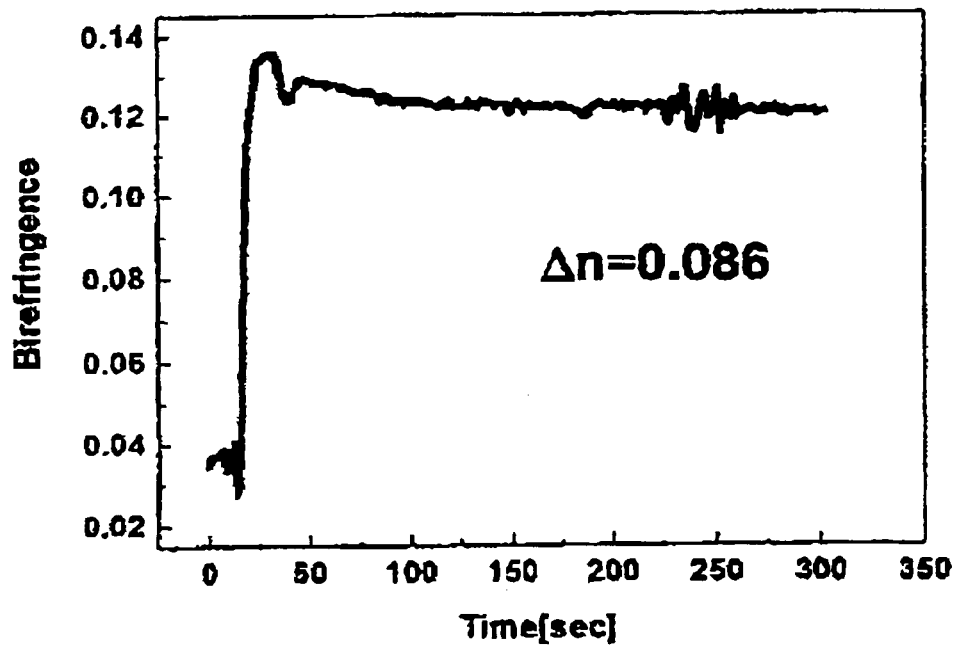
FIG. 8 is a diagram showing the photoresponsive properties of the homopolymer of the invention of Example 21.
Figure 9:
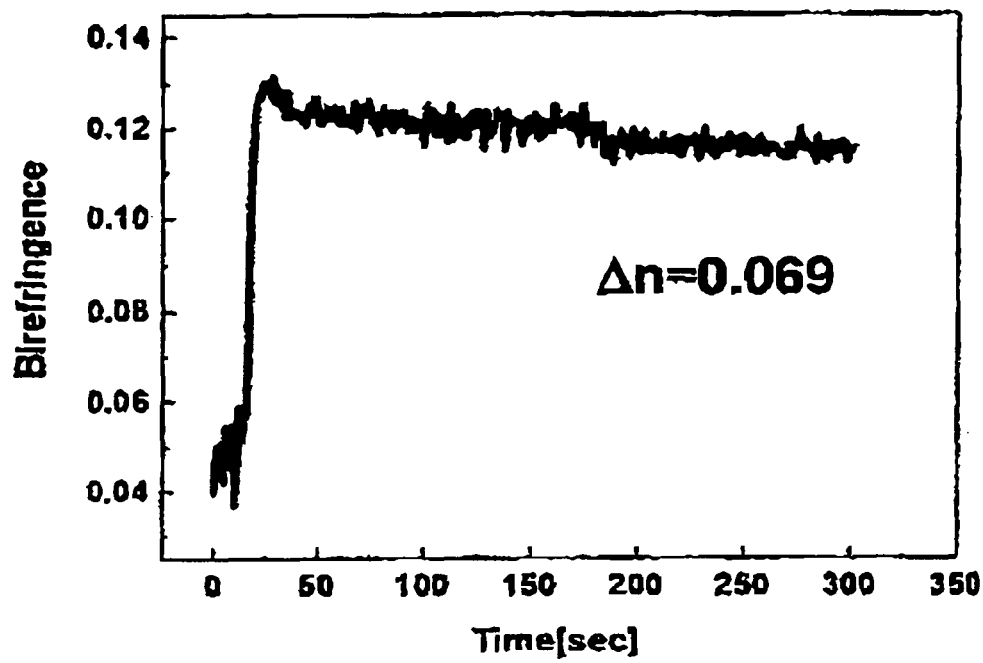
FIG. 9 is a diagram showing the photoresponsive properties of the cyanobenzene homopolymer for comparison with FIG. 8.

FIGS. 8 and 9 show the photoresponsive properties of the respective homopolymers. Each sample was obtained by spin-coating a 1-mm-thick glass substrate with a THF solution of each homopolymer (5 wt %) at 700 revolutions/minute.

From FIGS. 8 and 9, it was found that each polymer showed a rapid increase in the photo-induced birefringence value immediately after the exciting light irradiation and then the photo-induced birefringence value was stabilized at a constant value (about 0.069 and about 0.086 per 1 μm-thick film). Further, it was found that, when the exciting light irradiation was stopped, the cyanoazobenzene homopolymer showed a slight decrease in the photo-induced birefringence value, however, the homopolymer of the invention did not show a decrease in the photo-induced birefringence value. Further, the photo-induced birefringence value of the homopolymer of the invention is a large value which was 1.25 times as large as that of cyanoazobenzene homopolymer. The chemical structures of the respective polymers are similar and there is a slight difference in the structure that one of the benzene rings was replaced with a pyridine ring. However, as the photoresponsive dynamics shown here, the achievement of increase in the photo-induced birefringence value and reduction of relaxation clearly show the effect of introduction of a heterocycle.

Example 22

A copolymer represented by the following formula of the monomer constituting the homopolymer of the invention in Example 21 and a monotolan monomer (copolymerization ratio of 1:1 and 2:1) was evaluated with respect to photoresponsive properties.

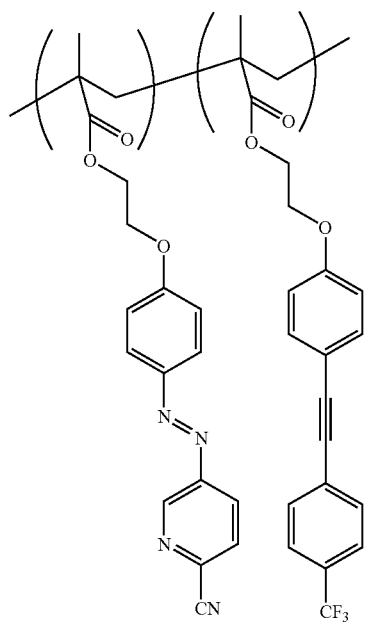

The optical system for evaluation and measurement conditions were the same as Example 20.

Figure 10:
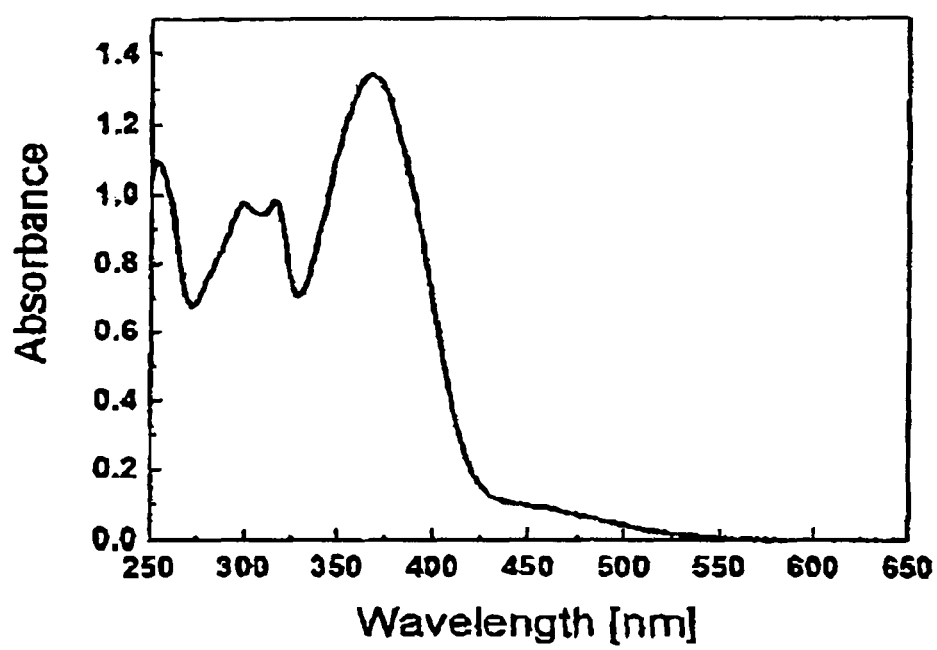
FIG. 10 is the absorption spectrum of the 2:1 copolymer of Example 22.

The absorption spectrum of the 2:1 copolymer ($3.3 \times 10^{-6}$ mol/L in $CHCl_3$) is shown in FIG. 10.

Each sample was obtained by spin-coating a 1-mm-thick glass substrate with a dichloromethane solution of each copolymer (5 wt %) at 700 revolutions/minute.

Figure 11:
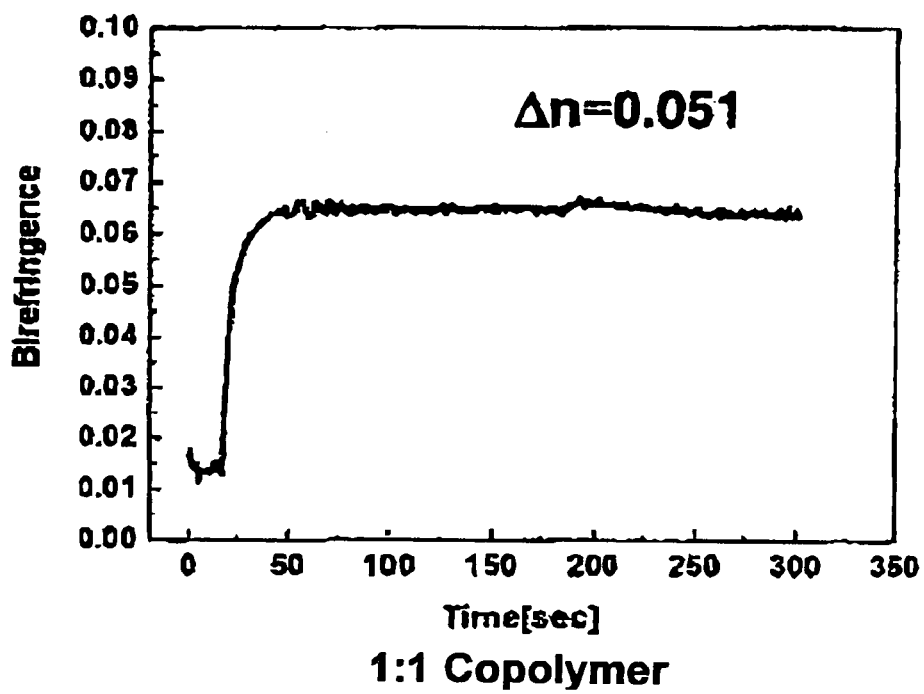
FIG. 11 is a diagram showing the photo-induced birefringence dynamics of the 1:1 copolymer of Example 22.
Figure 12:
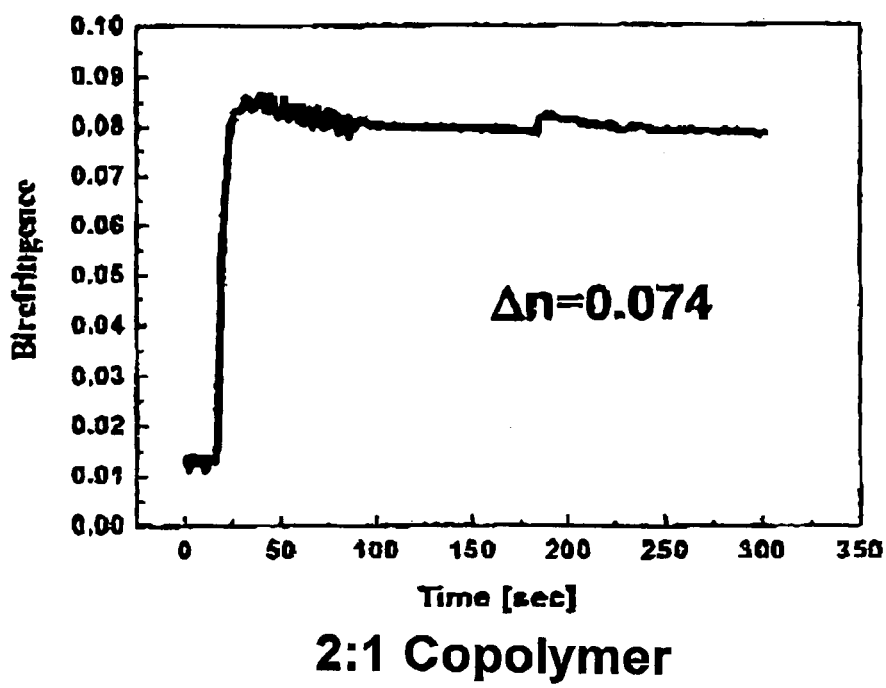
FIG. 12 is a diagram showing the photo-induced birefringence dynamics of the 2:1 copolymer of Example 22.

The respective photo-induced birefringence dynamics thereof are shown in FIGS. 11 and 12.

From FIGS. 11 and 12, it was found that each polymer showed a rapid increase in the photo-induced birefringence value immediately after the exciting light irradiation and then the photo-induced birefringence value was stabilized at a constant value (about 0.051 and about 0.074 per 1 μm-thick film). Further, it was found that, when the exciting light irradiation was stopped, the polymers did not show any decrease in the photo-induced birefringence value, and the photo-induced birefringence value was stable. These values were a little lower than that of the homopolymer of the invention of Example 21, however, when they were calculated in terms of the introduction amount of dye, they rather increased. Therefore, it is considered that a high-performance material with lower absorption was obtained by copolymerizing a tolan unit which has large molecular birefringence and is completely transparent within the visible range of spectrum. With the use of such a material with low absorption, even if a thick film is formed, the properties of the film is not deteriorated, therefore, it is also an extremely preferable property from the viewpoint of application thereof to memory for practical purposes.

Example 23

In the same manner, a copolymer represented by the following formula of the monomer constituting the homopolymer of the invention in Example 21 and a bistolan monomer (copolymerization ratio of 1:1) was evaluated with respect to photoresponsive properties.

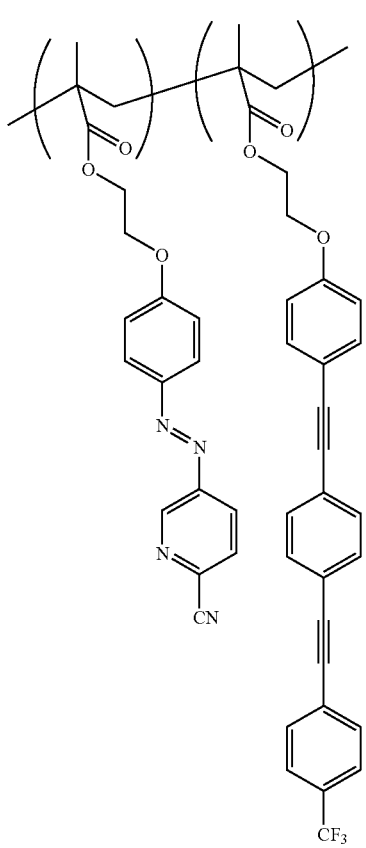

Figure 13:
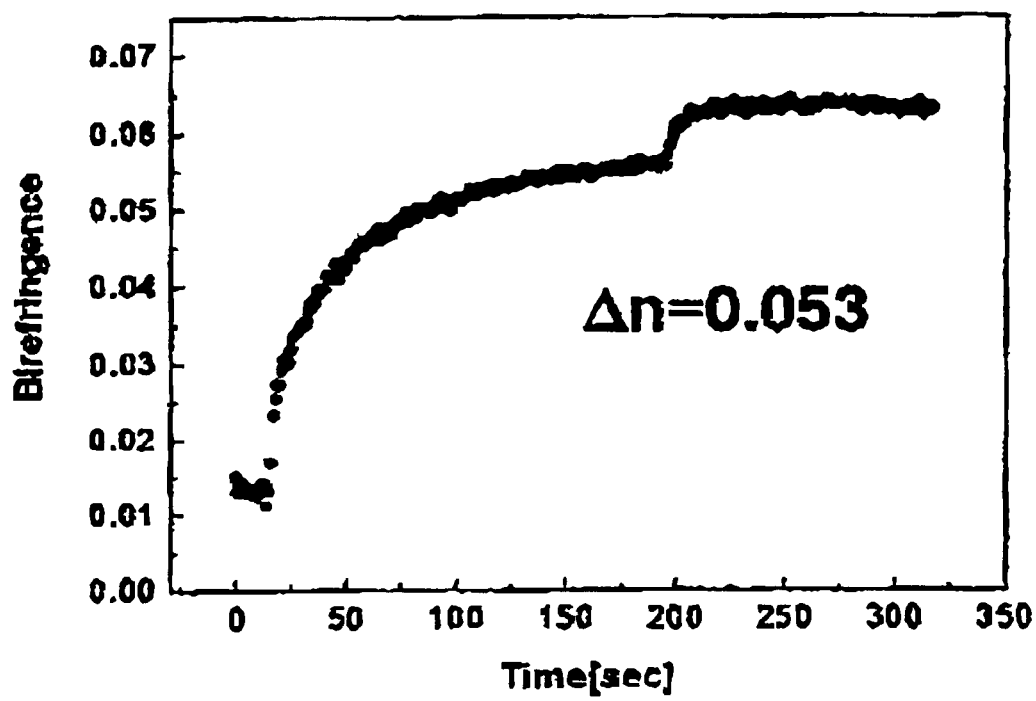
FIG. 13 is a diagram showing the photo-induced birefringence dynamics of the copolymer of Example 23.

The photo-induced birefringence dynamics of the copolymer are shown in FIG. 13. In the same manner as the case of the 1:1 copolymer of Example 22, it was found that the copolymer showed a photo-induced birefringence value of about 0.053 per 1 μm-thick film. Further, it was found that the copolymer did not show relaxation (although a little signal change was observed immediately after the light was blocked). From the viewpoint of introduction amount of dye, the copolymer exerted equivalent photo-induced birefringence with a smaller introduction amount of dye than that of the monotolan copolymer, therefore, it is also an extremely preferable property from the viewpoint of application thereof to memory for practical purposes.

Example 24

A copolymer represented by the following formula (x:y:z 1:1:1) was evaluated in the same manner with respect to photoresponsive properties.

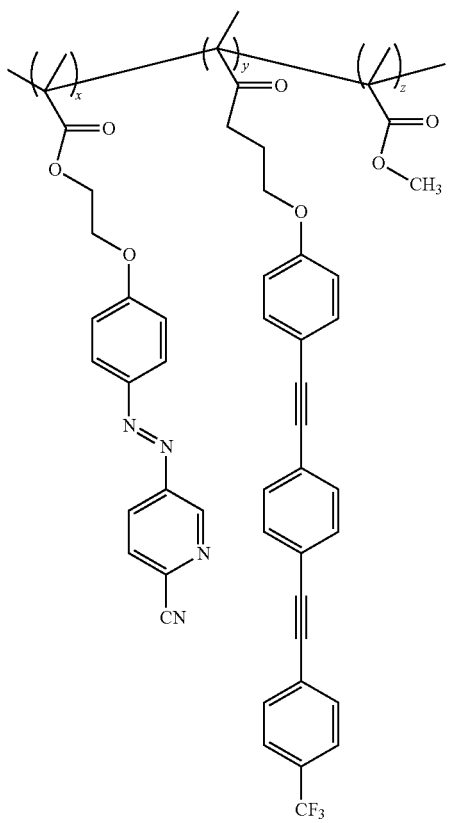

Figure 14:
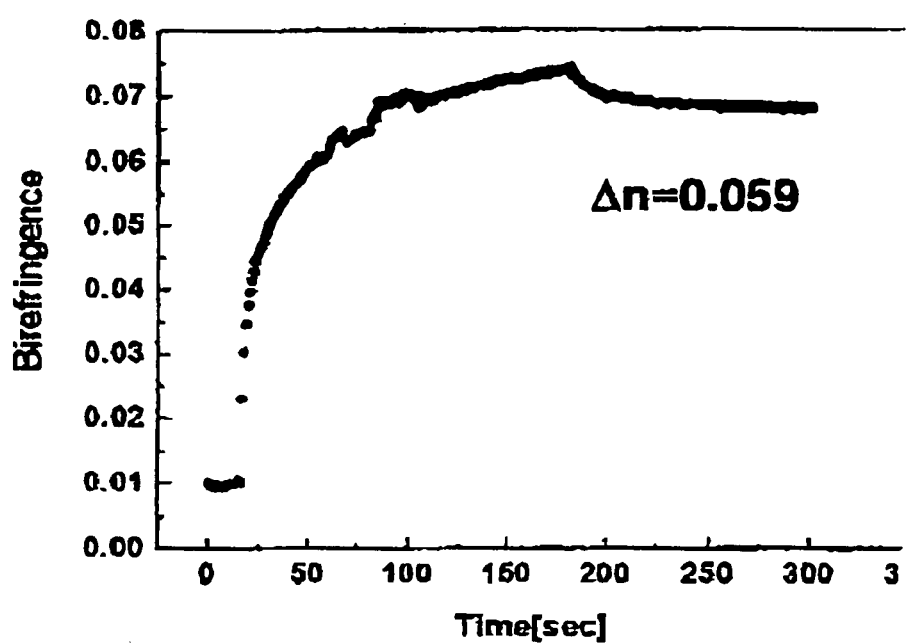
FIG. 14 is a diagram showing the photo-induced birefringence dynamics of the copolymer of Example 24.

The photo-induced birefringence dynamics of the copolymer are shown in FIG. 14.

It was found that the copolymer showed a large photo-induced birefringence value of about 0.059 per 1 μm-thick film and a slight relaxation (although a little signal change was observed immediately after the light was blocked). It is considered that these results are attributable to the pasticization effect of the system due to the introduction of a methylmethacrylate monomer. On the contrary, from the viewpoint of introduction amount of dye, by introducing a methylmethacrylate monomer unit, the copolymer exerted equivalent photo-induced birefringence with a smaller introduction amount of dye than that of the monotolan copolymer, therefore, it is also an extremely preferable property from the viewpoint of application thereof to memory for practical purposes.

Example 25

Synthesis examples of the compounds with a tolan structure and a bistolan structure to be used in Examples 22 to 24 are described.

1) Synthesis of Methacrylate Monomer with Tolan Structure 1.10 g (5 mmol) of 4-iodophenol, 0.935 g (5.5 mmol) of 4-ethynyl-α,α,α-rifluorotoluene, 0.019 g of copper iodide, 0.289 g of a palladium catalyst (Pd(PPh$_3$)$_4$) were dissolved in a mixed solvent of 200 ml of triethylamine and 10 ml of THF and reacted at room temperature for 10 hours or more. The reaction product was extracted with ether and subjected to separation and purification by column chromatography to obtain 1.31 g of a product.

To 1.31 g (5 mmol of the obtained product and 1.25 g (10 mmol) of 2-bromoethanol, 138 g (10 mmol) of potassium carbonate was added, and the mixture was refluxed in acetone for 72 hours. The reaction product was extracted with ether and subjected to separation and purification by column chromatography to obtain 0.82 g of a compound with a structure represented by the following formula as a white solid.

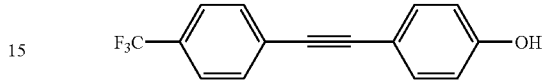

0.755 g (2.5 mmol) of the resultant white solid was reacted with 0.523 g (5 mmol) of methacryloyl chloride in the presence of 0.506 g (5 mmol) of triethylamine. After completion of the reaction, the resultant solution was subjected to extraction using chloroform, and recrystallization from methanol to obtain 0.61 g of a white solid.

Figure 15:
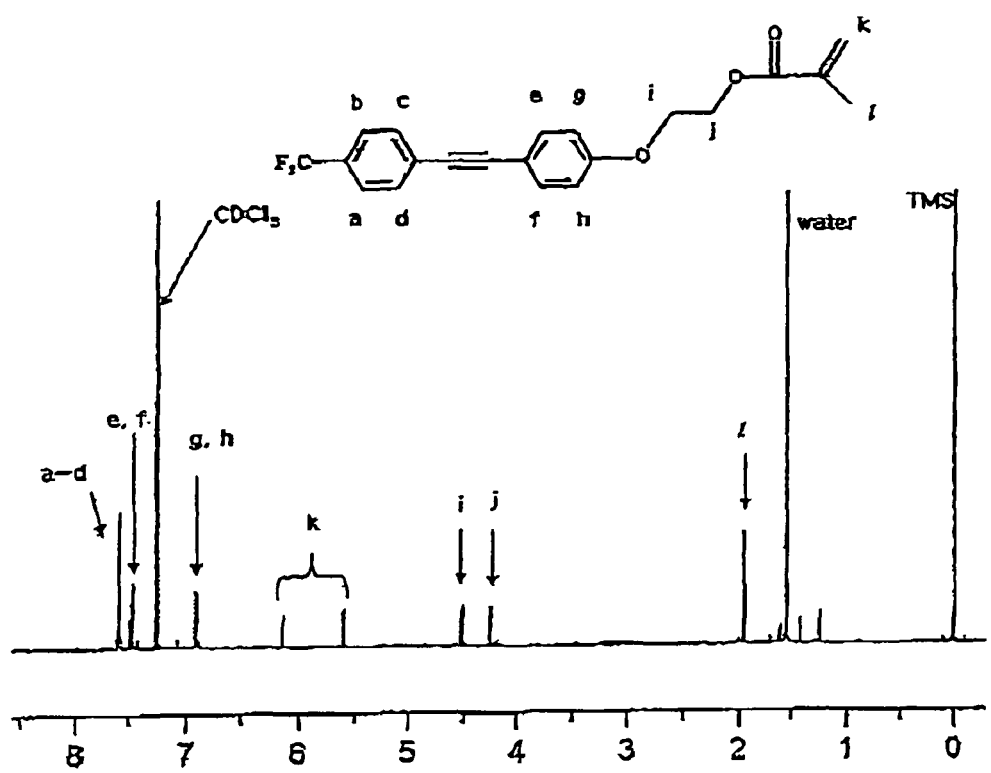
FIG. 15 is the $^1$H-NMR spectrum and the absorption spectrum of the monomer of the synthesis 1) in Example 25.
Figure 15:
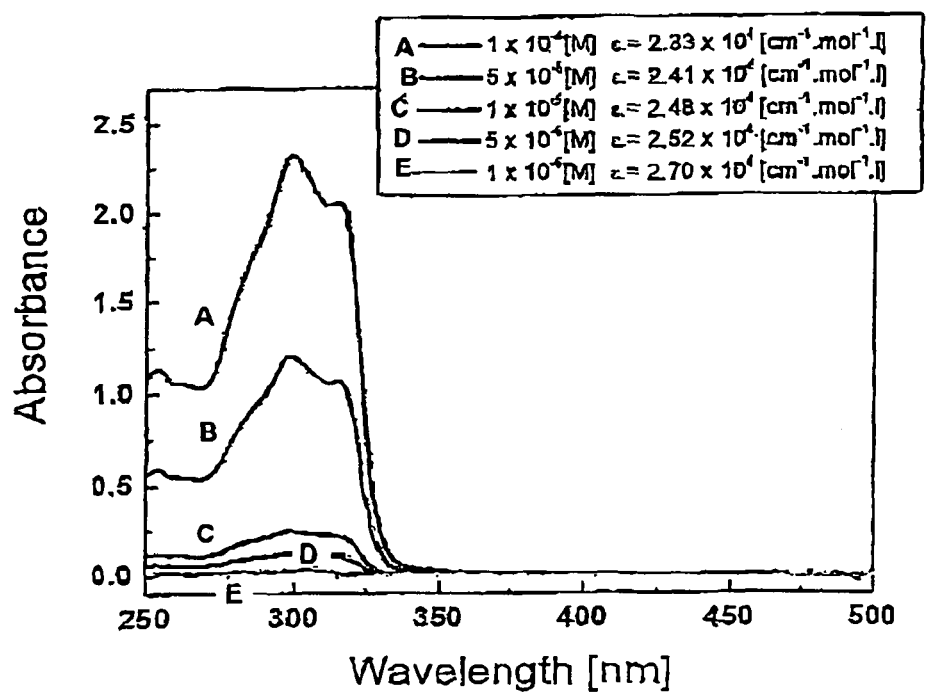

The obtained white solid is a monomer with a structure of the following structure and the $^1$H-NMR spectrum and absorption spectrum of the monomer are shown in FIG. 15.

The polymerization method for obtaining a random copolymer of this monomer and a methacrylate monomer of a heterocyclic azo compound is in accordance with the method described above.

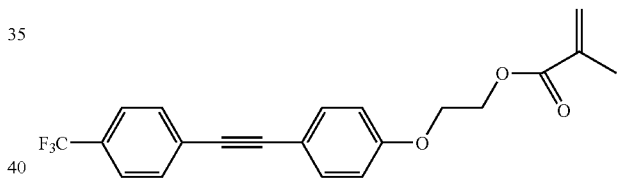

2) Synthesis of Methacrylate Monomer with Bistolan Structure 1.10 g (5 mmol) of 4-iodophenol, 0.996 g (5.5 mmol) of 1-bromo-4-ethynylbenzene, 0.019 g of copper Iodide, 0.289 g of a palladium catalyst (Pd(PPh$_3$)$_4$) were dissolved in a mixed solvent of 200 ml of triethylamine and 10 ml or THF and reacted at room temperature for 10 hours or more. The reaction product was extracted with ether and subjected to separation and purification by column chromatography to obtain 1.27 g of a product of the following formula.

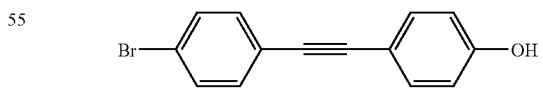

0.68 g (2.5 mmol) of the above compound, 0.45 mlg (2.76 mmol) of 4-ethynyl-α,α,α-trifluorotoluene, 0.009 g of copper iodide, 0.145 g of a palladium catalyst (Pd(PPh$_3$)$_4$) were dissolved in 100 ml of triethylamine and reacted at 90° C. for 2 hours or more. The reaction product was extracted with ether and subjected to separation and purification by column chromatography to obtain 0.79 g of a compound of the following formula.

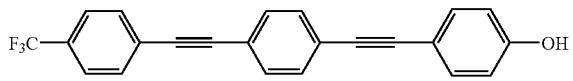

To 0.995 g (2.64 mmol) of the above compound and 0.55 ml (7.76 mmol) of 2-bromoethanol, 0.725 g (5.25 mmol) of potassium carbonate was added, and the mixture was refluxed in butanone for 72 hours. The reaction product was extracted with ether and subjected to separation and purification by column chromatography to obtain 0.50 g of a compound of the following formula as a white solid.

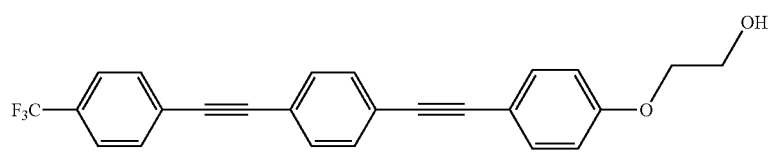

0.354 g (0.87 mmol) of the obtained white solid was reacted with 0.135 g (1.29 mmol) of methacryloyl chloride in the presence of 0.36 ml (2.85 mmol) of triethylamine. After completion of the reaction, the resultant solution was subjected to extraction using chloroform, and recrystallization from methanol to obtain 0.21 g of a compound of the following formula as a white solid.

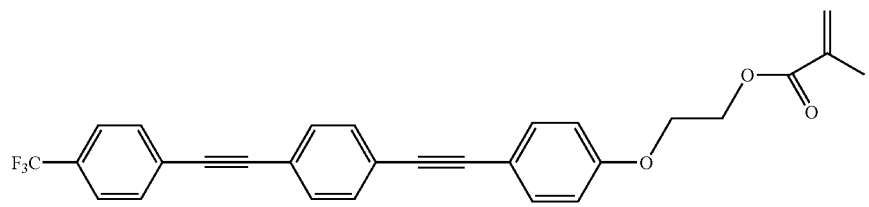

Example 26

A 1:1 copolymer with a cyanobiphenyl monomer represented by the following formula was evaluated in the same manner with respect to photoresponsive properties.

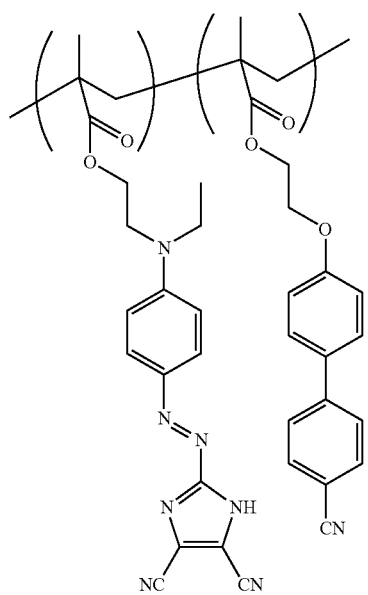

Figure 16:
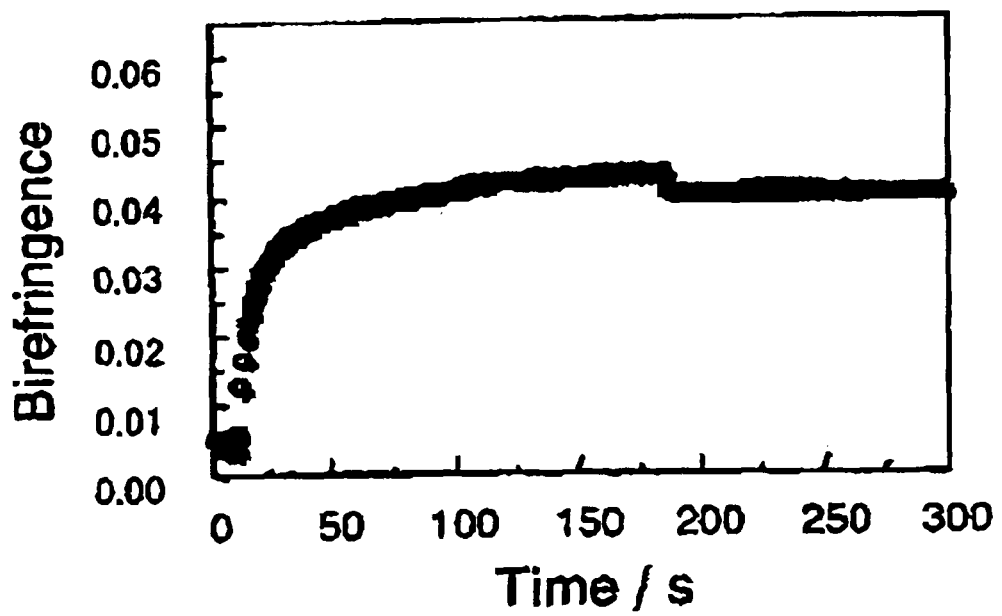
FIG. 16 is a diagram showing the photo-induced birefringence dynamics of the copolymer of Example 26.

FIG. 16 shows the photo-induced birefringence dynamics of the copolymer.

It was found that the copolymer showed a photo-induced birefringence value (about $0.035/\mu m$) about 3 times as large as that of Polymer (2) (1:1 copolymer) in Example 20. Also, it was found that the relaxation immediately after the light was blocked was improved by about 4 times, i.e., from about 23% to about 5%. It is considered that this is attributable to the effect on stabilization of orientation based on the liquid crystallinity of the cyanobiphenyl group introduced as a copolymerization component. Further, from the viewpoint of introduction amount of dye, the copolymer exerted about 3 times photo-induced birefringence with a smaller introduction amount of dye than that of the 1:1 copolymer (the above Polymer 2) of Molecule (2) and a methylmethacrylate monomer, therefore, it is also an extremely preferable property from the viewpoint of application thereof to memory for practical purposes.

Example 27

Figure 17:
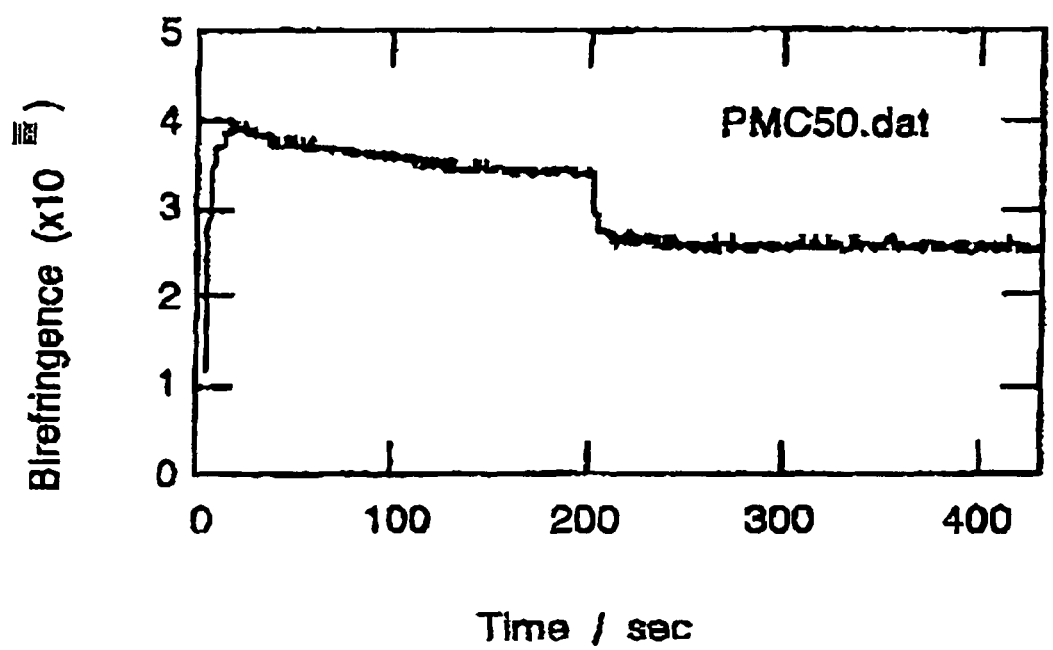
FIG. 17 is a diagram showing the birefringence change of Polymer 3 of Example 27.
Figure 18:
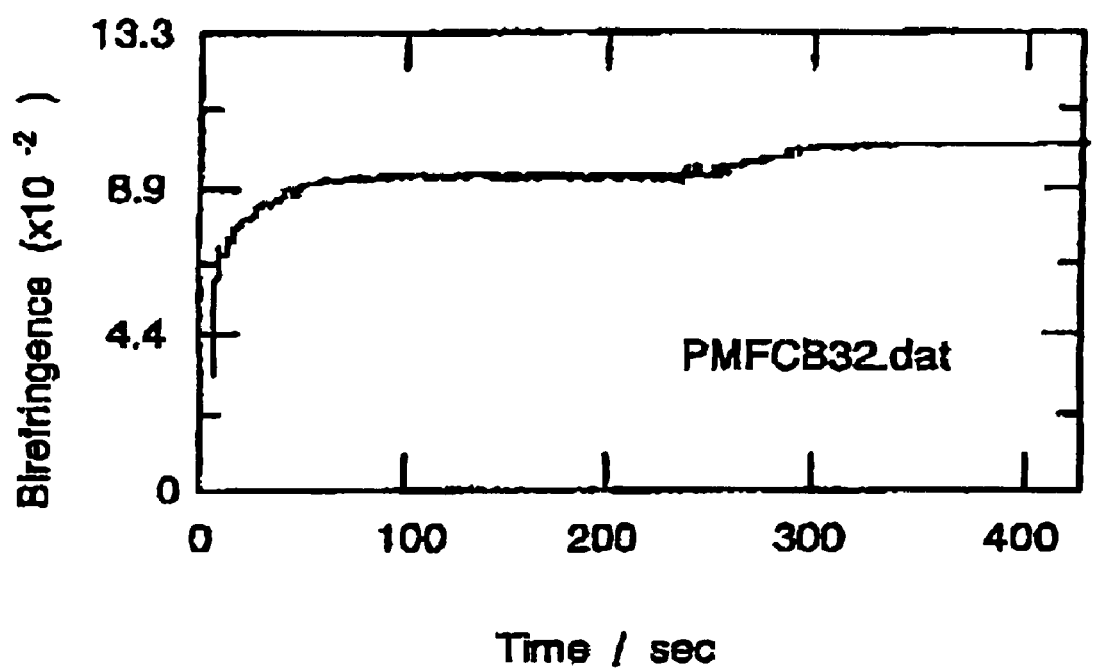
FIG. 18 is a diagram showing the birefringence change of Polymer 4 of Example 27.

In the same manner, polymers 3, 4 and 5 represented by the following formulae were compared and effects of the introduction of a copolymerization component with large birefringence on properties were examined. The results are shown in FIG. 17 and FIG. 18.

Polymer 3

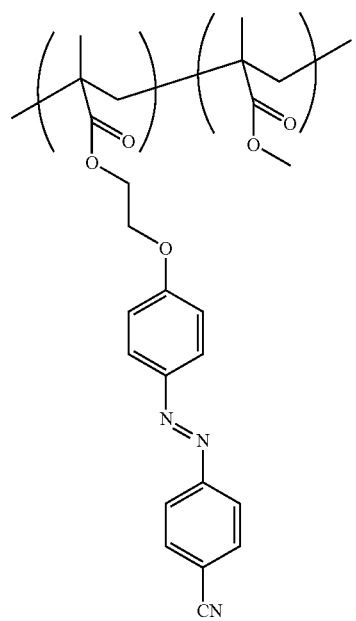

Polymer 5

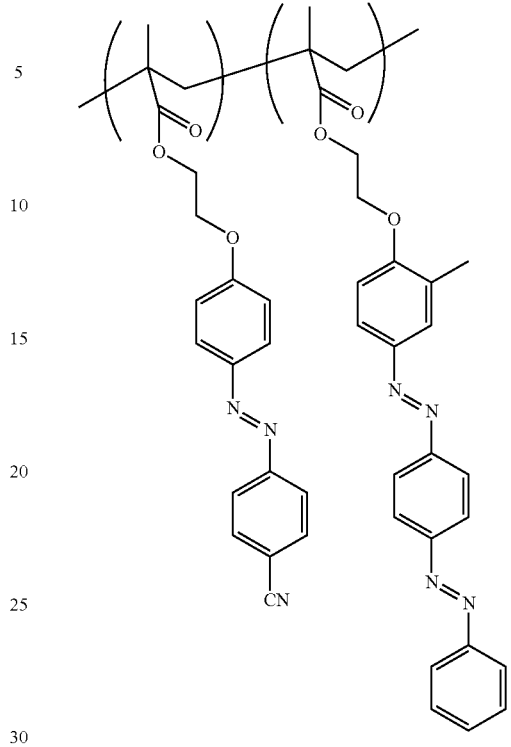

Polymer 4

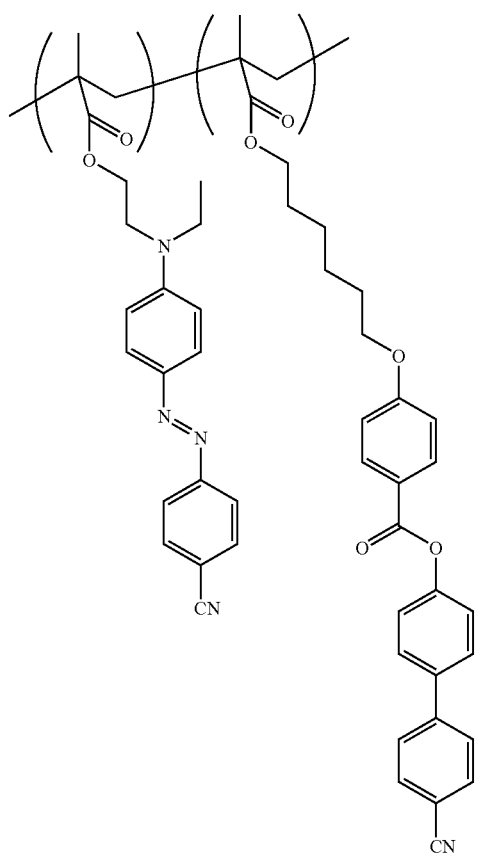

As shown in FIG. 17, Polymer 3 made a relatively good response immediately after the exciting light irradiation, however, when the exciting light irradiation was stopped, it was relaxed by about 30% rapidly to show a photo-induced birefringence value of approximately 0.025. Further, it was found that, when the exciting light irradiation was stopped, a decrease in about 50% of photo-induced birefringence value was observed. On the contrary, as shown in FIG. 18, it was found that a novel compound of Polymer 4 did not show the rapid increase and decrease immediately after the exciting light irradiation unlike Polymer 3, and made a stable and rapid response. Further, relaxation of the photo-induced birefringence value after the exciting light irradiation was stopped was hardly observed, in fact, a little increase thereof was observed, and it was shown that by the introduction of a comonomer component with a large dielectric anisotropy (high birefringence), a large photo-induced birefringence value of about 0.1 was obtained with remarkably excellent stability though Polymers had a photoresponsive moiety with the same chemical structure.

The comonomers as the copolymerization components for increasing the photo-induced birefringence may be synthesized by, for example, the following steps.

(1: Example of Compound Having Connected Two Azo Groups)

71.0 g (3.16 mmol) of Disperse Yellow, 0.79 g (632 mmol) of 2-bromoethanol, and 0.87 g (6.32 mmol) of potassium carbonate were dissolved in 50 ml of acetone, and reacted at 50° C. for 72 hours. Then, the mixture was air-cooled to the room temperature, extracted using 100 ml of chloroform and 100 ml of a saturated aqueous potassium carbonate solution, and extracted using 200 ml of chloroform and 200 ml of aqueous sodium chloride solution. The resultant solution washed with distilled water twice, and subjected to a filtration. The obtained powder was subjected to recrystallization from ethanol to obtain Molecule (9) of the following formula with a yield of 74%

0.288 g (0.8 mmol) of the obtained Molecule (9) and 0.162 g (1.6 mmol) of triethylamine were dissolved in dichloromethane and stirred in an ice bath. 0.167 g (1.6 mmol) of methacryloyl chloride was slowly added dropwise thereto and stirred overnight. After completion of the reaction, the mixture washed with an aqueous potassium carbonate solution, a saturated sodium chloride solution, and distilled water, and extracted with chloroform. The solvent was distilled off under reduced pressure to obtain Molecule (10) of the following formula as brown powder.

Figure 19:
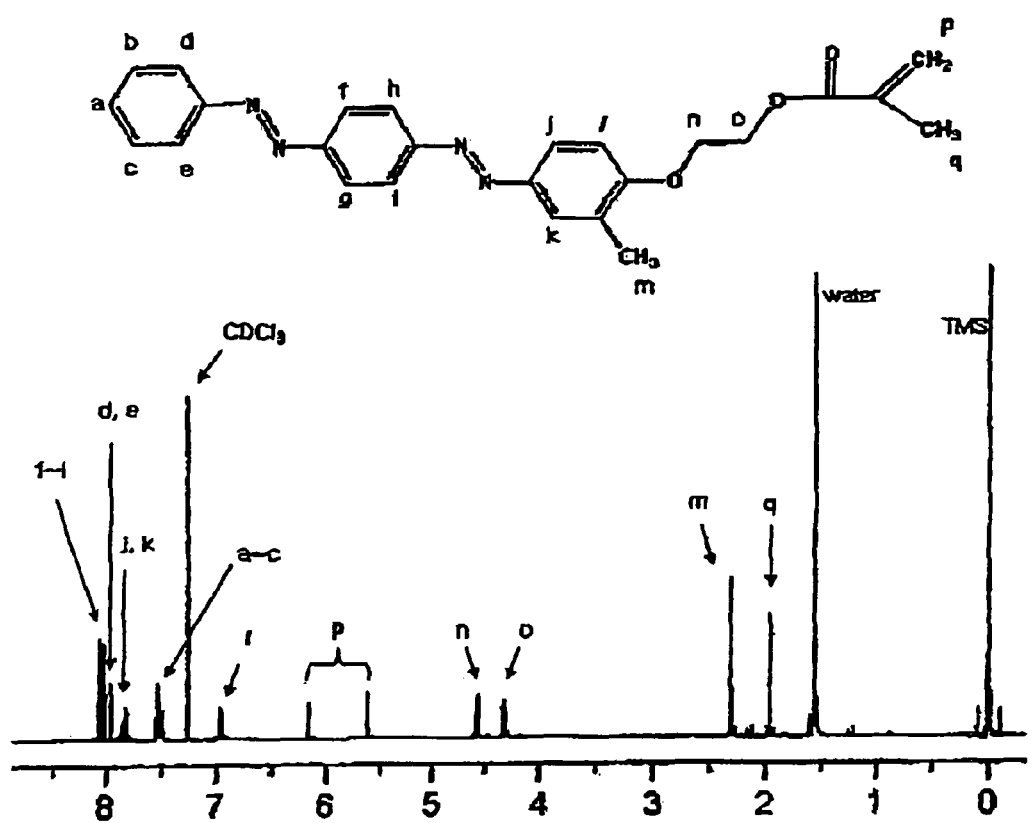
FIG. 19 is the NMR spectrum of Molecule 10.
Figure 20:
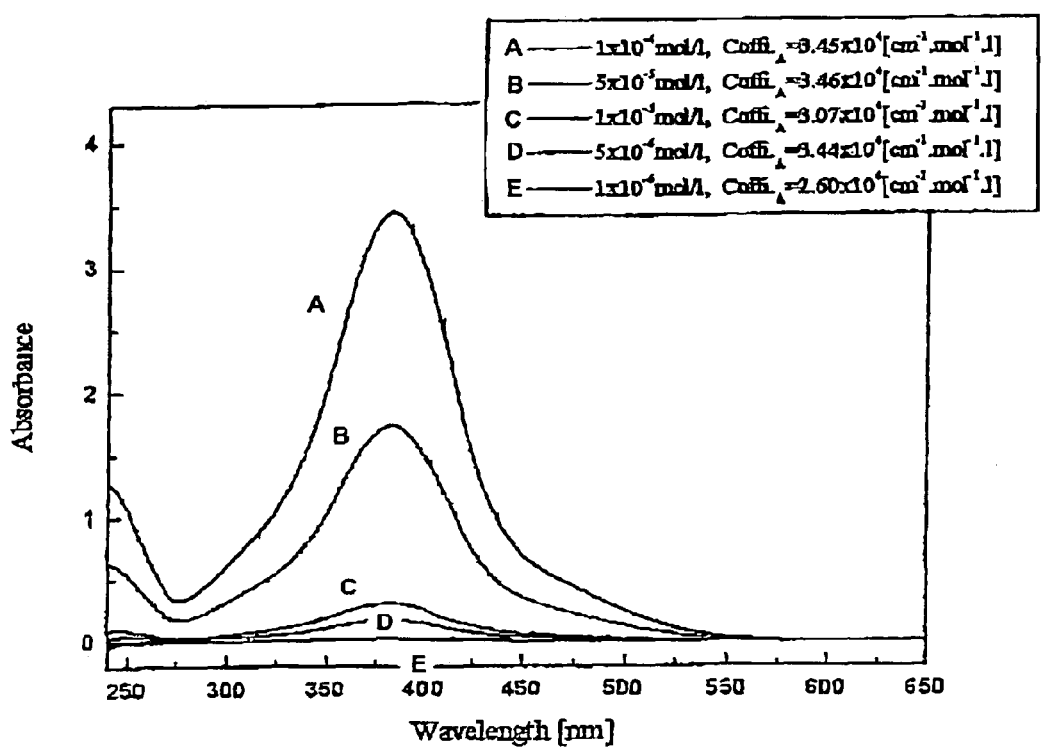
FIG. 20 is the UV-visible absorption spectrum of Molecule 10.

The NMR spectrum and ultraviolet-visible absorption spectrum of Molecule (10) are shown in FIGS. 19 and 20.

40 ml of 1,4-dioxane, 1.0 ml (7.7 mmol) of N,N-dimethylaniline, and a small amount of 2,6-di-tert-butyl-p-cresol were added to 1.67 g (7 mmol) of the obtained white solid. The mixture was kept at 60° C., and 0.6 ml (7.7 mmol) of acryloyl chloride was slowly added dropwise thereto and stirred for 2 hours. After completion of the reaction, the mixture was subjected to extraction using chloroform and recrystallization from a tetrahydrofuran/hexane mixed solvent, to obtain a white solid with a yield of 27.3%.

To 0.75 g (2.6 mmol) of the white solid were added a drop of dimethylformamide, 9.1 ml (130 mmol) of thionyl chloride, and a small amount of 2,6-di-tert-butyl-p-cresol. After

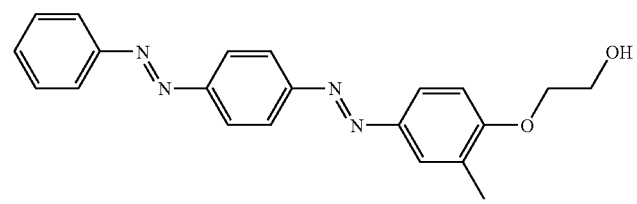

Molecule 9

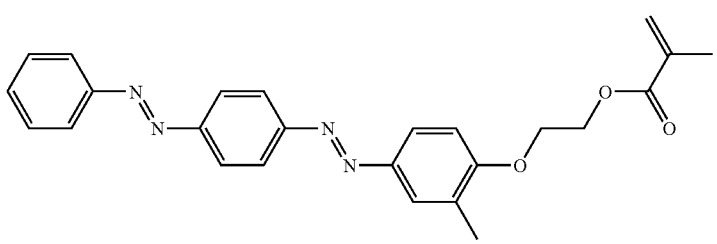

Molecule 10

The thus synthesized Molecule (10) was copolymerized with Molecule 2 described in Example 1 in the same manner as Example 1, to obtain a copolymer with increased photoinduced birefringence using Molecule (10) as an optically anisotropic group.

(2: Example of Compound Having Cyanobiphenyl Group)

35 ml of ethanol was added to 13.8 g (100 mmol of 4-hydroxybenzoic acid, and thereto was further added a solution prepared by dissolving 15.0 g (270 mmol) of potassium hydroxide and 1.0 g of potassium iodide in 15 ml of water. 14.6 ml (110 mmol) of 6-chloro-1-hexanol was added to the mixture dropwise and refluxed overnight. After the solvent was removed, the residue was dissolved in water, and hydrochloric acid was added thereto, and then, the resulting precipitates were isolated and washed with water. The precipitates were subjected to recrystallization from ethanol to obtain a white solid with a yield of 62.2%.

the mixture was stirred for 30 minutes in a water bath, 30 ml of tetrahydrofuran was added to the mixture. Then, a solution prepared by dissolving 0.5 g (2.6 mmol) of 4-hydroxy-4'-cyanobiphenyl and 1.8 ml (12.8 mmol) of triethylamine in 10 ml of tetrahydrofuran was added dropwise, and the resulting mixture was stirred overnight. The tetrahydrofuran was removed, and the residue was purified by column chromatography using a chloroform/ethyl acetate mixed solvent, to obtain white solid of Molecule (11) with a yield of 59%. The polymerization method for obtaining a random copolymer of Molecule 11 and a methacrylate monomer of an azo compound is in accordance with the method described above.

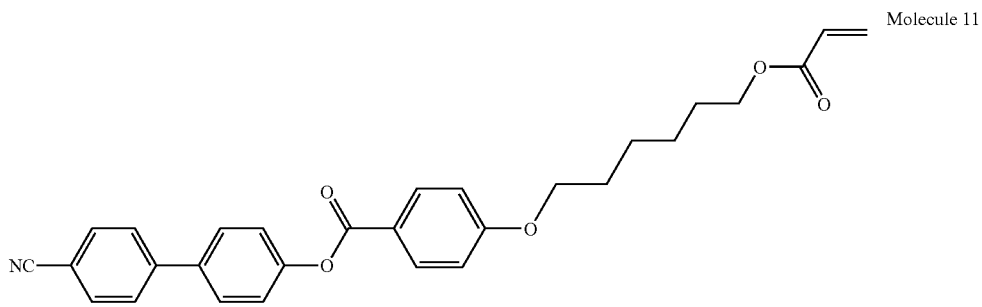

Molecule 11

Figure 21:
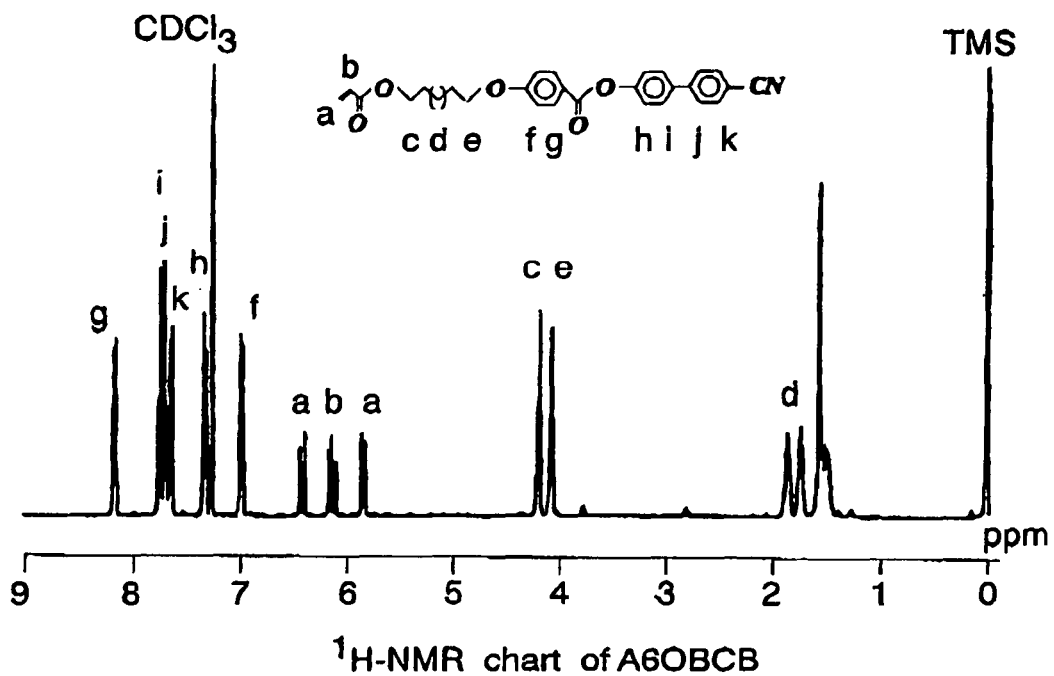
FIG. 21 is the NMR spectrum of Molecule 11.

The NMR data of Molecule 11 are shown in FIG. 21.

Further, the following example of synthesizing a compound having a cyanobiphenyl group is described.

That is, first, to 3.0 g (15 mmol) of 4-hydroxy(1,1'-biphenyl)-4-carbonitrile and 18.74 g (150 mmol) of 2-bromoethanol, 20.73 g (150 mmol) of potassium carbonate was added, and the mixture was refluxed in acetone for 48 hours. After the solvent was removed, the residue washed and dried to obtain 2.45 g of a light yellow solid.

2.0 g (8.36 mmol) of the obtained white solid was reacted with 1.06 ml (11 mmol) of methacryloyl chloride in the presence of 1.8 ml (13 mmol) of triethylamine. After completion of the reaction, the resultant solution was subjected to extraction using chloroform, and recrystallization from methanol to obtain 0.85 g of a white solid.

The $^1$H-NMR data of the obtained solid were as shown in Table 8.

TABLE 8

$^1$H NMR (δ[ppm], CDCl$_3$): 1.96 (t, 3H), 4.28 (t, 2H), 453 (t, 2H), 5.60 (q, 1H), 6.15 (d, 1H), 7.01 (t, 1H), 7.03 (t, 1H), 7.52 (t, 1H), 7.54 (t, 1H), 7.63 (d 1H), 7.65 (d, 1H), 7.68 (d, 1H), 7.71 (d, 1H).

Example 28

A 1:1 copolymer represented by the following formula of the methacrylate monomer of Molecule (6) of the above Example 6 and Molecule (10) was evaluated with respect to photoresponsive properties.

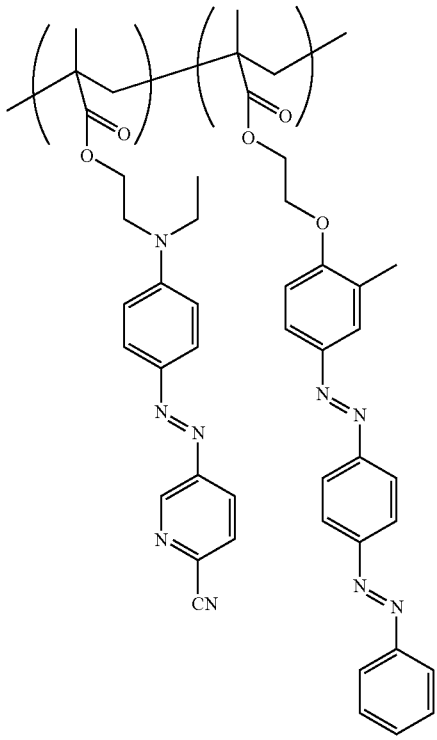

The optical system for evaluation and measurement conditions were the same as Example 20.

Figure 22:
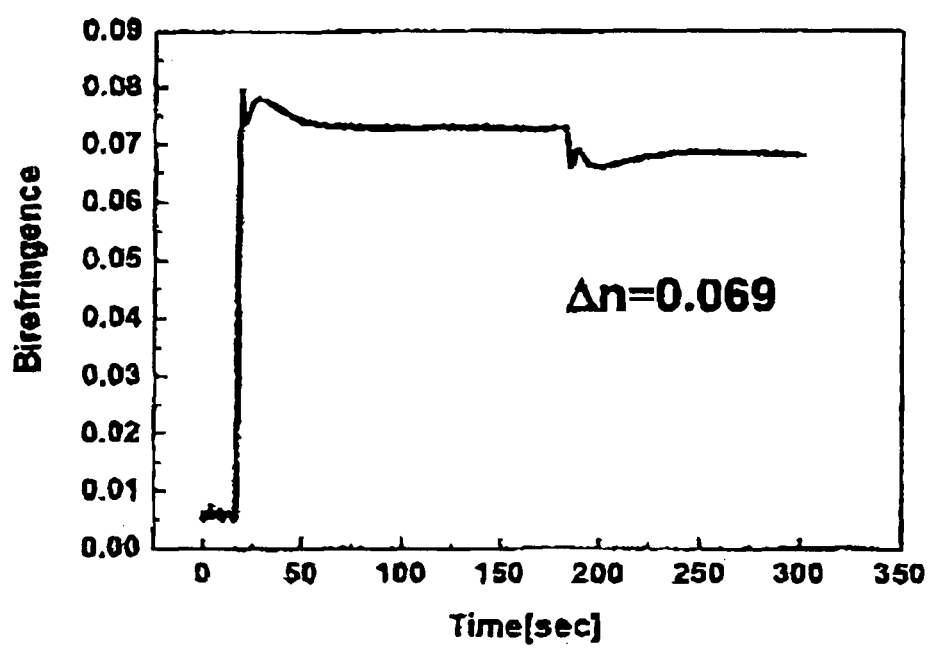
FIG. 22 is a diagram showing the photo-induced birefringence dynamics of the copolymer of Example 28.

FIG. 22 shows the photo-induced birefringence dynamics of the copolymer.

As shown in FIG. 22, it was found that the copolymer showed a rapid increase in the photo-induced birefringence value immediately after the exciting light irradiation and then the photo-induced birefringence value was stabilized at a constant value (about 0.069 per 1 μm). Further, it was found that, even if the exciting light Irradiation was stopped, the copolymer showed only a small decrease of about 5% in the photo-induced birefringence value.

Example 29

A 1:1 copolymer represented by the following formula was evaluated in the same manner as above with respect to photoresponsive properties.

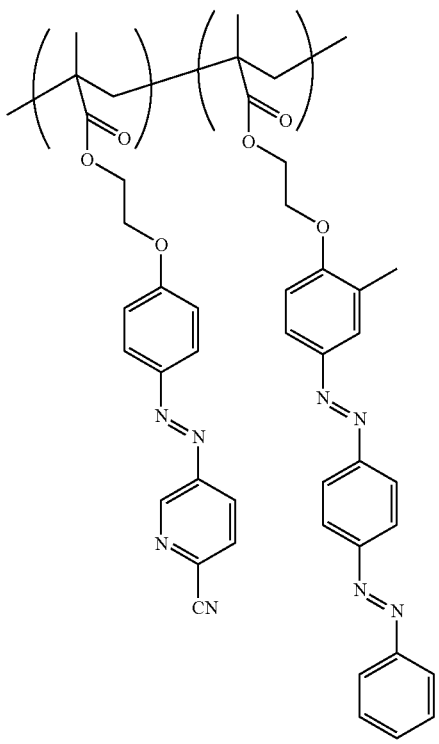

Figure 23:
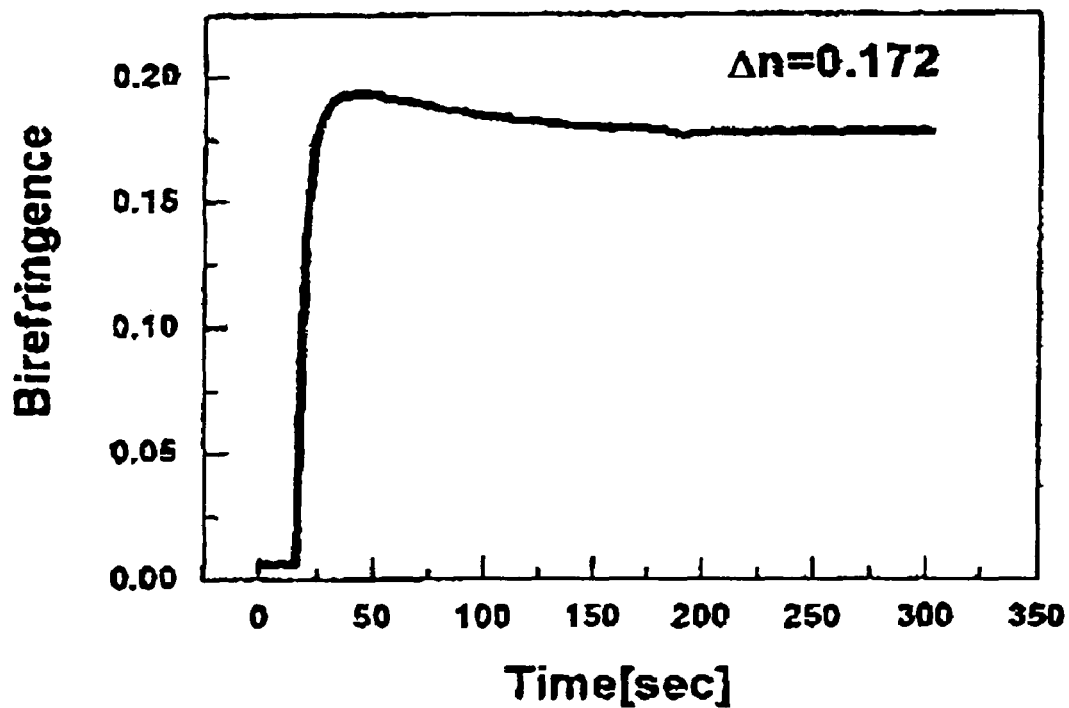
FIG. 23 is a diagram showing the photo-induced birefringence dynamics of the copolymer of Example 29.

FIG. 23 shows the photo-induced birefringence dynamics of the copolymer.

As shown in FIG. 23, it was found that the copolymer made an extremely rapid initial response and showed an extremely large photo-induced birefringence value (about 0.172/1 μm) immediately after the exciting light irradiation. It is considered that this extremely large photo-induced birefringence value is attributable to the introduction of Molecule (10) with larger birefringence. Further, even if the exciting light irradiation was stopped, a decrease in the photo-induced birefringence value did not occur, therefore, it is considered that the copolymer is one of the materials with a favorable property.

Example 30

A 1:1 copolymer represented by the following formula of the above Molecule (2) and Molecule 10 was evaluated in the same manner with respect to photoresponsive properties.

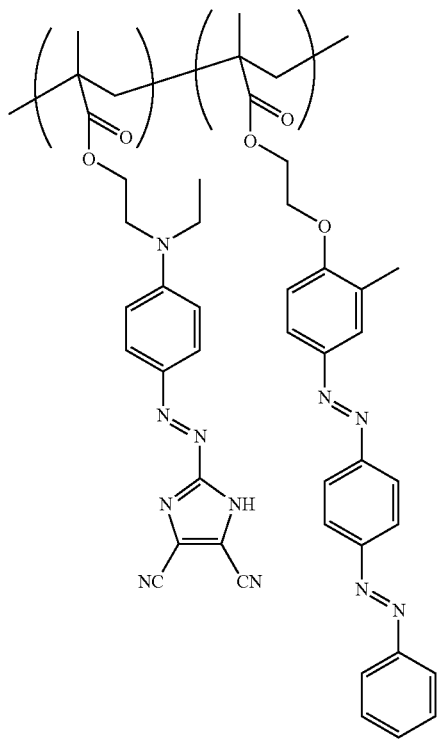

Figure 24:
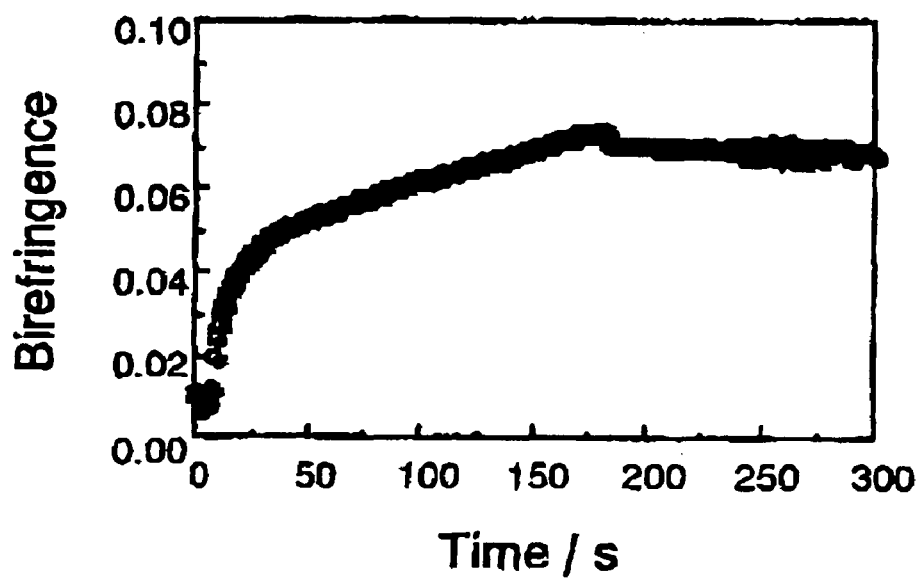
FIG. 24 is a diagram showing the photo-induced birefringence dynamics of the copolymer of Example 30.

FIG. 24 shows the photo-induced birefringence dynamics of the copolymer.

This copolymer showed a photo-induced birefringence value (about 0.061/μm) about 5 times as large as that of the 1:1 copolymer (Polymer 2) of Molecule (2) and the methylmethacrylate monomer. Even if it is compared with the photo-induced birefringence value of the 1:1 copolymer of Molecule 2 and the cyanobiphenyl methylmethacrylate monomer, about 1.7 times improvement was achieved. Further, also the relaxation immediately after the light was blocked was about 7%, which showed that the improvement was achieved. However, it was found that the responsiveness was slightly delayed. It is considered that thus was attributable to the large molecular birefringence and motility of Molecule (10) introduced as a copolymerization component.

INDUSTRIAL APPLICABILITY

According to the present invention as described above, compared with the prior art, various holographic optical information recording properties such as sensitivity, response speed, long-term storage stability, and repeatability can be significantly improved and increased, and there is provided the high-performance optical information recording material or medium.

What is claimed is:

1. A photoresponsive heterocyclic azo oligomer or polymer having a photoresponsive moiety in at least one of the main chain and side chain, the photoresponsive moiety being a building block represented by the following formula (1):

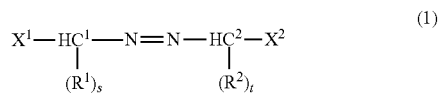

wherein $HC^1$ and $HC^2$ each represent a ring structure, at least one of them being a heterocyclic structure selected from the group consisting of a pyrazole and a pyridine, $R^1$ and $R^2$ each represent a hydrogen atom or a substituent connected to the ring structure and may be the same or different ones, s and t each represent the number thereof, and $X^1$ and $X^2$ each represent a terminal group or a linking group, at least one of them being a linking group connected to the main chain of the oligomer or polymer and the terminal group being a cyano group, wherein the side chain is a monotolan or bistolan optically anisotropic group.

2. The photoresponsive heterocyclic azo oligomer or polymer according to claim 1, wherein both $HC^1$ and $HC^2$ are a pyrazole or a pyridine.

3. The photoresponsive heterocyclic azo oligomer or polymer according to claim 1, wherein the linking group is selected from the group consisting of ester, thioester, ether, thioether, amine, amide, sulfone, sulfonyl, sulfonamide, imine, azo, and hydrocarbon chain groups, and combinations thereof.

4. The photoresponsive heterocyclic azo oligomer or polymer according to claim 1, wherein the oligomer or polymer connected to the linking group has the main chain of a carbon chain and the side chain having the building block represented by the formula (1).

5. The photoresponsive heterocyclic azo oligomer or polymer according to claim 4, wherein the carbon chain of the main chain is formed by polymerization of a monomer having the building block represented by the formula (1) and a polymerizable group or by copolymerization of the monomer and another monomer having a polymerizable group.

6. The photoresponsive heterocyclic azo oligomer or polymer according to claim 5, wherein the carbon chain is formed by polymerization or copolymerization of a monomer represented by the following formula (2):

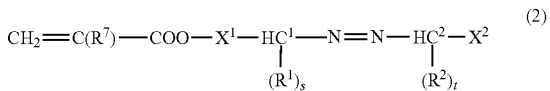

wherein $HC^1$ and $HC^2$ each represent a ring structure selected from the group consisting of a pyrazole and a pyridine, $R^1$ and $R^2$ each represent a hydrogen atom or a substituent connected to the ring structure and may be the same or different ones, s and t each represent the number thereof, $X^1$ represents a linking group and $X^2$ represents a terminal group, the linking group being connected to the main chain of the oligomer or polymer, the terminal group being a hydrogen atom or a substituent, and $R^7$ represents a hydrogen atom or a methyl group.

7. A method for producing the photoresponsive heterocyclic azo oligomer or polymer according to claim 1, comprising: polymerizing a polymerizable monomer or oligomer for connecting the building block of formula (1) with the linking group.

8. A method for producing the photoresponsive heterocyclic azo oligomer or polymer according to claim 1, comprising: reacting a compound having a reactive moiety for linking the building block of formula (1) with an oligomer or polymer.

9. A method for producing the photoresponsive heterocyclic azo oligomer or polymer according to claim 1, comprising: copolymerizing a polymerizable monomer or oligomer for linking the building block of formula (1) with one or more monomers or oligomers having the optically anisotropic group.

10. A method for producing the photoresponsive heterocyclic azo oligomer or polymer according to claim 1, comprising: reacting a compound having the optically anisotropic group, with an oligomer or polymer having the building block of formula (1) in at least one of the main chain and side chain.

11. An optical information recording material comprising the photoresponsive heterocyclic azo oligomer or polymer according to claim 1, wherein the material records an optical information utilizing change of an optical absorption property or refractive index by light irradiation or localized heating, and the material uses the building block represented by the formula (1) as a photoresponsive moiety.

12. The optical information recording material according to claim 11, wherein the material is used as a rewritable volume hologram memory.

13. The optical information recording material according to claim 11, wherein the material is used as a rewritable surface relief memory.

14. The photoresponsive heterocyclic azo oligomer or polymer according to claim 1, wherein the side chain is a bistolan optically anisotropic group.

* * * * *